(12) United States Patent
Jensen et al.

(10) Patent No.: US 6,235,898 B1
(45) Date of Patent: May 22, 2001

(54) PROCESS FOR THE SYNTHESIS OF CARBAPENEM INTERMEDIATED AND COMPOUNDS PRODUCED

(75) Inventors: Mark S. Jensen, Holmdel; Chunhua Yang, Edison; Nobuyoshi Yasuda, Mountainside, all of NJ (US)

(73) Assignee: Merck & Co., Inc., Rahway, NJ (US)

( * ) Notice: Subject to any disclaimer, the term of this patent is extended or adjusted under 35 U.S.C. 154(b) by 0 days.

(21) Appl. No.: 09/511,958

(22) Filed: Feb. 23, 2000

Related U.S. Application Data

(62) Division of application No. 09/159,158, filed on Sep. 23, 1998, now Pat. No. 6,048,978.
(60) Provisional application No. 60/061,233, filed on Oct. 7, 1997.

(51) Int. Cl.[7] .............................. C07D 477/06; C07F 7/22
(52) U.S. Cl. ........................................... 540/302; 540/465
(58) Field of Search ..................... 540/302, 465

(56) References Cited

U.S. PATENT DOCUMENTS 4,108,990    8/1978    Plum et al. ..................... 424/245

OTHER PUBLICATIONS

S. M. Schmitt et al., *J. Antibiotics*, 41(6), p. 70787 (1988).
E. Vedejs et al., *JACS*, 114, pp. 6556–6558 (1992).
U.Kolb, et al., *Organometallics*, 14(6), p. 2827–2834 (1995).
K. Jurkschat et al., *J Organometallic Chem.*, 290(3), p. 285–289 (1985).
K. Jurkschat et al., *J Organometallic Chem.*, 272, pp. C13–C16 (1984).

*Primary Examiner*—Richard L. Raymond
*Assistant Examiner*—Thomas McKenzie
(74) *Attorney, Agent, or Firm*—Sylvia A. Ayler; Mark R. Daniel

(57) ABSTRACT

A process of synthesizing a carbapenem compound of formula 6:

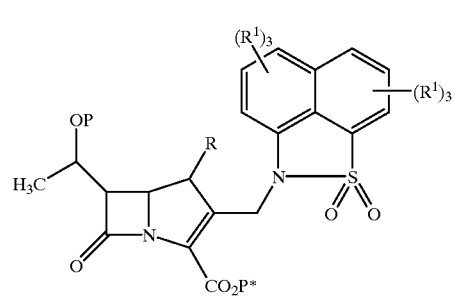

is disclosed using a compound of formula 4':

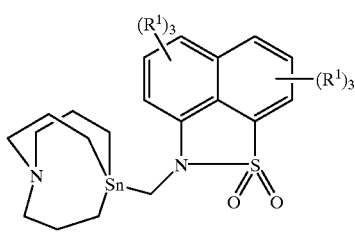

The intermediate compounds that are described herein are also included in the present invention.

13 Claims, No Drawings

PROCESS FOR THE SYNTHESIS OF CARBAPENEM INTERMEDIATED AND COMPOUNDS PRODUCED

This application is a divisional of U.S. Ser. No. 09/159,158, filed Sep. 23, 1998 and U.S. Pat. No. 6,048,978 granted Apr. 11, 2000, which claims the benefit of U.S. Provisional Application No. 60/061,233, filed Oct. 7, 1997.

BACKGROUND OF THE INVENTION

The present invention relates to a process for synthesizing carbapenem intermediates. Generally the carbapenems are substituted at the 2-position. The intermediate compounds are included as well.

Many of the carbapenems are useful against gram positive microorganisms, especially methicillin resistant Staphylococcus aureus (MRSA), methicillin resistant Staphylococcus epidermidis (MRSE), and methicillin resistant coagulase negative Staphylococci (MRCNS). These antibacterials thus comprise an important contribution to therapy for treating infections caused by these difficult to control pathogens. There is an increasing need for agents effective against such pathogens (MRSA/MRCNS) which are at the same time relatively free from undesirable side effects.

SUMMARY OF THE INVENTION

In one aspect of the invention, a process of synthesizing a carbapenem compound of formula 6:

is disclosed wherein
R represents H or methyl, P and P* represent protecting groups and each $R^1$ represents H, halo, OH, OP wherein P is a protecting group, $—C_{1-6}$ straight- or branched-chain alkyl, unsubstituted or substituted with one to four $R^d$ groups; and $—C_{3-7}$ cycloalkyl, unsubstituted or substituted with one to four $R^d$ groups;

each $R^d$ independently represents halo; OP, wherein P is a protecting group, —CN; $—NO_2$; $—NR^eR^f$; $—OR^g$; $—SR^g$; $—CONR^eR^f$; $—COOR^g$; $—SOR^g$; $—SO_2R^g$; $—SO_2NR^eR^f$; $—NR^eSO_2R^f$; $—COR^e$; $—NR^eCOR^f$; $—OCOR^e$; $—OCONR^eR^f$; $—NR^eCONR^fR^g$; $—NR^eCO_2R^h$; $—OCO_2R^h$; $—C(NR^e)NR^fR^g$; $—NR^eC(NH)NR^fR^g$; $—NR^eC(NR^f)R^g$; —R* or —Q;

$R^e$, $R^f$ and $R^g$ represent hydrogen; —R*; $—C_{1-6}$ straight- or branched-chain alkyl unsubstituted or substituted with one to four $R^i$ groups;

or $R^e$ and $R^f$ taken together with any intervening atoms represent a 4–6 membered saturated ring optionally interrupted by one to three of O, S, —C(O)— or $NR^g$ with $R^g$ as defined above, said ring being unsubstituted or substituted with one to four $R^i$ groups;

each $R^i$ independently represents halo; —CN; $—NO_2$; phenyl; $—NHSO_2R^h$; $—OR^h$, $—SR^h$; $—N(R^h)_2$; $—N^+(R^h)_3$; $—C(O)N(R^h)_2$; $—SO_2N(R^h)_2$; heteroaryl; heteroarylium; $—CO_2R^h$; $—C(O)R^h$; $—OCOR^h$; $—NHCOR^h$; guanidinyl; carbamimidoyl or ureido;

each $R^h$ independently represents hydrogen, a $—C_{1-6}$ straight or branched-chain alkyl group, a $—C_3–C_6$ cycloalkyl group or phenyl, or when two $R^h$ groups are present, said $R^h$ groups may be taken in combination and represent a 4–6 membered saturated ring, optionally interrupted by one or two of O, S, $SO_2$, —C(O)—, NH and $NCH_3$;

Q is selected from the group consisting of:

wherein:
a and b are 1, 2 or 3;
$L^-$ is a pharmaceutically acceptable counterion;
α represents O, S or $NR^s$;
β, δ, λ, μ and σ represent $CR^t$, N or $N^+R^s$, provided that no more than one of β, δ, λ, μ and σ is $N^+R^s$;
R* is selected from the group consisting of:

wherein:
d represents O, S or $NR^k$;
e, g, x, y and z represent $CR^m$, N or $N^+R^k$, provided that no more than one of e, g, x, y and z in any given structure represents $N^+R^k$;

$R^k$ represents hydrogen; $—C_{1-6}$ straight- or branched-chain alkyl, unsubstituted or substituted with one to four $R^i$ groups; or $—(CH_2)_nQ$ where n=1, 2 or 3 and Q is as previously defined;

each $R^m$ independently represents a member selected from the group consisting of: hydrogen; halo; —CN; $—NO_2$; $—NR^nR^o$; $—OR^n$; $—SR^n$; $—CONR^nR^o$; $—COOR^h$; $—SOR^n$; $—SO_2R^n$; $—SO_2NR^nR^o$; $—NR^nSO_2R^o$; $—COR^n$; $—NR^nCOR^o$; $—OCOR^n$; $—OCONR^nR^o$; $—NR^nCO_2R^h$; $—NR^nCONR^oR^h$; $—OCO_2R^h$; $—CNR^nNR^oR^h$; $—NR^nCNHNR^oR^h$; $—NR^nC(NR^o)R^h$; $—C_{1-6}$ straight- or branched-chain alkyl, unsubstituted or substituted with one to four $R^i$ groups; $—C_{3-7}$ cycloalkyl, unsubstituted or substituted with one to four $R^i$ groups; and $—(CH_2)_nQ$ where n and Q are as defined above;

$R^n$ and $R^o$ represent hydrogen, phenyl; $—C_{1-6}$ straight- or branched-chain alkyl unsubstituted or substituted with one to four $R^i$ groups;

each $R^s$ independently represents hydrogen; phenyl or $—C_{1-6}$ straight- or branched-chain alkyl, unsubstituted or substituted with one to four $R^i$ groups;

each $R^t$ independently represents hydrogen; halo; phenyl; —CN; $—NO_2$; $—NR^uR^v$; $—OR^u$; $—SR^u$; $—CONR^uR^v$; $—COOR^h$; $—SOR^u$; $—SO_2R^u$; $—SO_2NR^uR^v$; $—NR^uSO_2R^v$; $—COR^u$; $—NR^uCOR^v$; $—OCOR^u$; $—OCONR^uR^v$; $—NR^uCO_2R^v$; $—NR^uCONR^vR^w$; $—OCO_2R^v$; $—C_{1-6}$ straight- or branched-chain alkyl, unsubstituted or substituted with one to four $R^i$ groups;

$R^u$ and $R^v$ represent hydrogen or —$C_{1-6}$ straight- or branched-chain alkyl, unsubstituted or substituted with one to four $R^i$ groups;

or $R^u$ and $R^v$ together with any intervening atoms represent a 4–6 membered saturated ring optionally interrupted by one or more of O, S, $NR^w$ or —C(O)—, said ring being unsubstituted or substituted with one to four $R^i$ groups;

each $R^w$ independently represents hydrogen; —$C_{1-6}$ straight- or branched-chain alkyl, unsubstituted or substituted with one to four $R^i$ groups; $C_{3-6}$ cycloalkyl optionally substituted with one to four $R^i$ groups; phenyl optionally substituted with one to four $R^i$ groups, or heteroaryl optionally substituted with 1–4 $R^i$ groups;

or $R^h$ and $R^w$ taken together with any intervening atoms represent a 5–6 membered saturated ring, optionally interrupted by one or two of O, S, $SO_2$, NH or $NCH_3$;

$R^x$ represents hydrogen or a $C_{1-8}$ straight- or branched-chain alkyl, optionally interrupted by one or two of O, S, SO, $SO_2$, $NR^w$, $N^+R^hR^w$, or —C(O)—, said chain being unsubstituted or substituted with one to four of halo, CN, $NO_2$, $OR^w$, $SR^w$, $SOR^w$, $SO_2R^w$, $NR^hR^w$, $N^+(R^h)_2R^w$, —C(O)—$R^w$, C(O)$NR^hR^w$, $SO_2NR^hR^w$, $CO_2R^w$, OC(O)$R^w$, OC(O)$NR^hR^w$, $NR^hC(O)R^w$, $NR^hC(O)NR^hR^w$, or a phenyl or heteroaryl group which is in turn optionally substituted with from one to four $R^i$ groups or with one to two $C_{1-3}$ straight- or branched-chain alkyl groups, said alkyl groups being unsubstituted or substituted with one to four $R^i$ groups;

$R^y$ and $R^z$ represent hydrogen; phenyl; —$C_{1-6}$ straight or branched chain alkyl, unsubstituted or substituted with one to four $R^i$ groups, and optionally interrupted by O, S, $NR^w$, $N^+R^hR^w$ or —C(O)—;

or $R^x$ and $R^y$ together with any intervening atoms represent a 4–6 membered saturated ring optionally interrupted by O, S, $SO_2$, $NR^w$, $N^+R^hR^w$ or —C(O)—, unsubstituted or substituted with 1–4 $R^i$ groups, and when $R^x$ and $R^y$ together represent a 4–6 membered ring as defined above, $R^z$ is as defined above or $R^z$ represents an additional saturated 4–6 membered ring fused to the ring represented by $R^x$ and $R^y$ taken together, optionally interrupted by O, S, $NR^w$ or —C(O)—, said rings being unsubstituted or substituted with one to four $R^i$ groups comprising reacting a compound of formula 4':

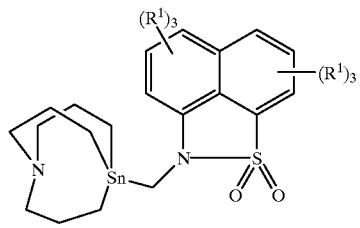

4' with a carbapenem of formula 7:

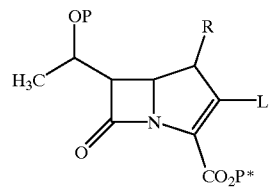

7 wherein R, P and P* are as previously defined and L represents a leaving group, to produce a compound of formula 6.

DETAILED DESCRIPTION OF THE INVENTION

The invention is described herein in detail using the terms defined below unless otherwise specified.

The term "alkyl" refers to a monovalent alkane (hydrocarbon) derived radical containing from 1 to 10 carbon atoms unless otherwise defined. It may be straight, branched or cyclic. Preferred alkyl groups include methyl, ethyl, propyl, isopropyl, butyl, t-butyl, cyclopentyl and cyclohexyl. When substituted, alkyl groups may be substituted with up to four substituent groups, selected from $R^d$ and $R^i$, as defined, at any available point of attachment. When the alkyl group is said to be substituted with an alkyl group, this is used interchangeably with "branched alkyl group".

Cycloalkyl is a specie of alkyl containing from 3 to 15 carbon atoms, without alternating or resonating double bonds between carbon atoms. It may contain from 1 to 4 rings which are fused.

The term "alkenyl" refers to a hydrocarbon radical straight, branched or cyclic containing from 2 to 10 carbon atoms and at least one carbon to carbon double bond. Preferred alkenyl groups include ethenyl, propenyl, butenyl and cyclohexenyl.

The term "alkynyl" refers to a hydrocarbon radical straight or branched, containing from 2 to 10 carbon atoms and at least one carbon to carbon triple bond. Preferred alkynyl groups include ethynyl, propynyl and butynyl.

Aryl refers to aromatic rings e.g., phenyl, substituted phenyl and the like, as well as rings which are fused, e.g., naphthyl, phenanthrenyl and the like. An aryl group thus contains at least one ring having at least 6 atoms, with up to five such rings being present, containing up to 22 atoms therein, with alternating (resonating) double bonds between adjacent carbon atoms or suitable heteroatoms. The preferred aryl groups are phenyl, naphthyl and phenanthrenyl. Aryl groups may likewise be substituted as defined. Preferred substituted aryls include phenyl and naphthyl.

Heteroaryl refers to a monocyclic aromatic hydrocarbon group having 5 or 6 ring atoms, or a polycyclic aromatic group having 8 to 16 atoms, containing at least one heteroatom, O, S, S(O), $SO_2$ or N, in which a carbon or nitrogen atom is the point of attachment, and in which one or two additional carbon atoms is optionally replaced by a heteroatom selected from O or S, and in which from 1 to 3 additional carbon atoms are optionally replaced by nitrogen heteroatoms, said heteroaryl group being optionally substituted as described herein. Examples of this type are pyrrole, pyridine, oxazole, thiazole and oxazine. Additional nitrogen atoms may be present together with the first nitrogen and oxygen or sulfur, giving, e.g., thiadiazole and the like.

Examples of polycyclic heteroaromatics include benzopyrans, benzofurans, benzopyrroles, benzimidazoles, benzothiazoles, quinolines, purines, isoquinolines, benzopyrimidines, dibenzofurans, dibenzothiophenes, 1,8-naphthosultams, The term "heterocycle" (heterocyclyl) refers to a 5–16 membered cycloalkyl group (nonaromatic) with 1–4 rings, in which one of the carbon atoms in the ring is replaced by a heteroatom selected from O, S or N, and in which up to three additional carbon atoms may be replaced by heteroatoms.

The term "heteroatom" means O, S, S(O), S(O)$_2$ or N, selected on an independent basis.

Heteroarylium refers to heteroaryl groups bearing a quaternary nitrogen atom and thus a positive charge. Examples include the following:

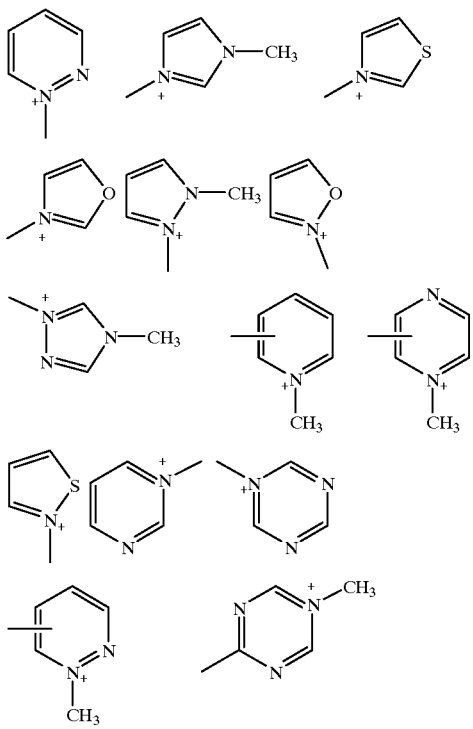

When a charge is shown on a particular nitrogen atom in a ring which contains one or more additional nitrogen atoms, it is understood that the charge may reside on a different nitrogen atom in the ring by virtue of charge resonance that occurs.

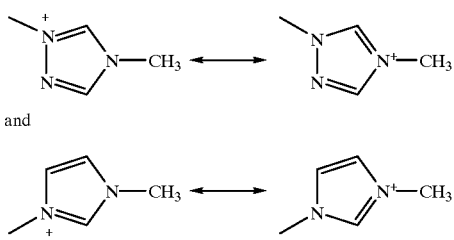

The term "heterocycloalkyl" refers to a cycloalkyl group (nonaromatic) in which one of the carbon atoms in the ring is replaced by a heteroatom selected from O, S or N, and in which up to three additional carbon atoms may be replaced by hetero atoms.

The terms "quaternary nitrogen" and "positive charge" refer to tetravalent, positively charged nitrogen atoms including, e.g., the positively charged nitrogen in a tetraalkylammonium group (e.g. tetramethylammonium), heteroarylium, (e.g., N-methyl-pyridinium), basic nitrogens which are protonated at physiological pH, and the like. Cationic groups thus encompass positively charged nitrogen-containing groups, as well as basic nitrogens which are protonated at physiologic pH.

The term "heteroatom" means O, S or N, selected on an independent basis.

Alkoxy refers to $C_1$–$C_4$ alkyl-O—, with the alkyl group optionally substituted as described herein.

L refers to a leaving group. Examples of suitable L groups are methanesulfonyl (mesyl or OMs), toluenesulfonyl (OTs), trifluoromethanesulfonyl (triflate or OTf), halo, and phosphonyl based groups like diphenylphosphonyl.

Halogen and "halo" refer to bromine, chlorine, fluorine and iodine. When the leaving group L is halo, this refers to Br, Cl and I.

M is H or a metal cation. Metal cation as used herein refers to Na, K, Mg, Zn and Li. Preferably, M is H or a metal cation selected from Na and K.

When a group is termed "protected" , such as by P, P*, P^, Y and the like, this means that the group is in modified form to preclude undesired side reactions at the protected site. Suitable protecting groups for the compounds of the present invention will be recognized from the present application taking into account the level of skill in the art, and with reference to standard textbooks, such as Greene, T. W. et al. *Protective Groups in Organic Synthesis* Wiley, New York (1991). Examples of suitable protecting groups are contained throughout the specification.

In some of the compounds of the present invention, P, P^. and P* represent hydroxyl and carboxyl protecting groups, respectively. Likewise, Y may represent a protecting group for X, which in turn represents O or N (see compound 4 below). These groups are generally removable, i.e., they can be removed, if desired, by procedures which will not cause cleavage or other disruption of the remaining portions of the molecule. Such procedures include chemical and enzymatic hydrolysis, treatment with chemical reducing or oxidizing agents under mild conditions, treatment with a transition metal catalyst and catalytic hydrogenation.

Examples of carboxyl protecting groups P* include allyl, benzhydryl, 2-naphthylmethyl, benzyl, silyl groups such as t-butyldimethylsilyl (TBDMS), trimethylsilyl, (TMS), triethylsilyl (TES), phenacyl, p-methoxybenzyl, o-nitrobenzyl, p-methoxyphenyl, p-nitrobenzyl, 4-pyridylmethyl and t-butyl.

Examples of suitable hydroxy protecting groups P and P^ include TMS, TES, TBDMS, o-nitrobenzyloxycarbonyl, p-nitrobenzyloxycarbonyl, benzyloxycarbonyl, allyloxycarbonyl, t-butyloxycarbonyl, 2,2,2-trichloroethyloxycarbonyl and the like.

Examples of suitable protecting groups Y for X equal to N include, for example, groups where the N is protected by or incorporated into a ring, such as by forming a piperidinyl group. Similarly, the N can be disubstituted to provide a nitrogen in protected form. In this instance, Y would represent disubstitution on the nitrogen atom.

When X represents O or NH, Y represents H or a protecting group as noted above. In the alternative, X and Y can be considered in combination to represent a ring system, containing from 1–4 rings comprised of from 5 to 16 atoms, 0 to 3 of which are N atoms, and 0 to 2 of which are selected from O, S, S(O) and S(O)$_2$. The ring system is aromatic, non-aromatic or partially aromatic and is unsubstituted or substituted with 1–3 groups selected from the group consisting of halo, OH, OP, $C_{1-6}$ alkyl, $C_{1-6}$ alkyl substituted with 1–3 of OH, OP, halo, $NH_2$, $NHC_{1-4}$ alkyl or $N(C_{1-4}$ alkyl)$_2$. Preferably X and Y are taken in combination to represent a ring system as defined above. The preferred ring system is a 1,8-naphthosultam, unsubstituted or substituted with 1–3 groups selected from C$_{1-6}$ alkyl unsubstituted or substituted with 1–3 of halo, OH or OP.

A preferred aspect of the invention relates to compounds of formulas 6, 4' and 5 wherein one R$^1$ represents a group which contains a positively charged moiety, and the remaining R$^1$ groups are selected from hydrogen and C$_{1-6}$ straight or branched chain alkyl, unsubstituted or substituted with one to four R$^d$ groups. More particularly, this subset of interest includes compounds of formulas 6, 4' and 5 wherein one R$^1$ represents a group containing a positively charged moiety and the remaining R$^1$ groups are hydrogen.

With respect to the positively charged moiety or moieties that are contained in one or more R$^1$ groups, it is preferred that from 1–3 positive charges be present, and most preferably two positive charges be present, balanced by a carboxylate anion and a negatively charged counterion.

Another preferred aspect is represented by formulas 6, 4' and 5 wherein one R$^1$ group represents a —C$_{1-6}$ straight or branched chain alkyl group, substituted with one to four R$^d$ groups, wherein one R$^d$ group represents —R* or Q. Hence, a positively charged moiety —R* or Q is attached to an alkyl group.

One aspect of the process that is of interest herein is the synthesis of a compound of formula 1:

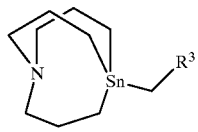

1 wherein R$^3$ is Cl, Br or I, which is comprised of reacting a compound of formula 2:

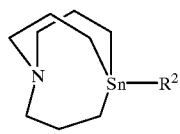

2 wherein R$^2$ is Cl, Br or I, with a compound of formula 3:

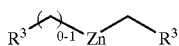

3 to produce a compound of formula 1.

Another aspect of the process that is of interest is the synthesis of a compound of formula 4:

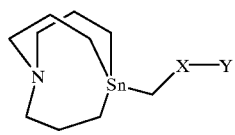

4 wherein
X represents O or NH and Y represents H or a protecting group, or in the alternative, X and Y taken in combination represent a ring system containing from 0–3 nitrogen atoms and 0–2 heteroatoms selected from O, S, S(O) and S(O)$_2$, said ring system having 1–4 rings, with from 5–16 atoms, said system being non-aromatic, partially aromatic or aromatic, and being unsubstituted or substituted with from 1–3 groups selected from halo, OH, OP, wherein P is a protecting group, C$_{1-6}$ alkyl and C$_{1-6}$ alkyl substituted with from 1–3 of halo, OH, OP, NH$_2$, NHC$_{1-4}$ alkyl and N(C$_{1-4}$ alkyl)$_2$ comprising reacting compound 1:

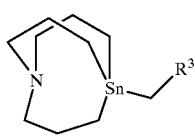

1 wherein R$^3$ is Cl, Br or I,
with a compound of the formula M—X—Y wherein M is H or a metal cation, and X and Y are as previously defined, to produce a compound of formula 4.

Another aspect of the process that is of particular interest is the synthesis of a compound of formula 4':

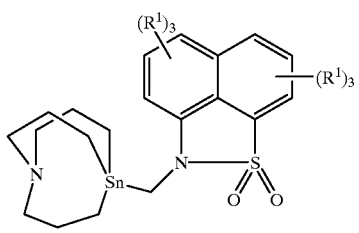

4' wherein each R$^1$ is as described above, comprising reacting a compound of formula 1:

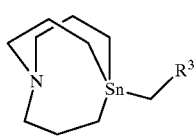

1 wherein R$^3$ is Cl, Br or I, with a naphthosultam of formula 5:

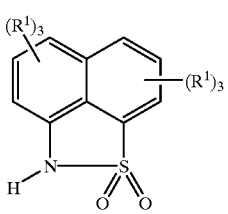

5 wherein R$^1$ is as previously defined, to produce a compound of formula 4'.

Another aspect of the process that is of interest is the synthesis of a carbapenem compound of formula 6:

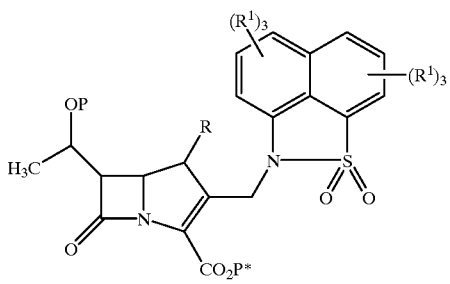

wherein R represents H or methyl, P and P* represent protecting groups and each $R^1$ is as described above, comprising reacting a compound of formula 4':

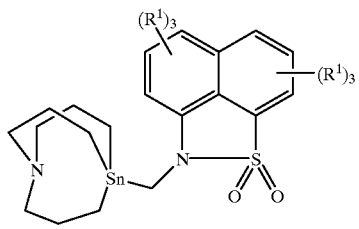

with a carbapenem of formula 7:

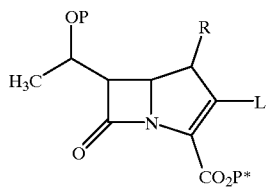

wherein R, P and P* are as previously defined and L represents a leaving group, to produce a compound of formula 6.

Another aspect of the process that is of particular interest is the synthesis of a compound of formula 4':

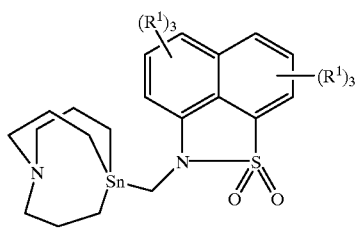

wherein each $R^1$ is as described above, comprising reacting a compound of formula 1:

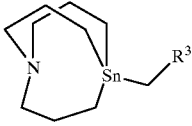

wherein $R^3$ is Cl, Br or I, with a naphthosultam of formula 5:

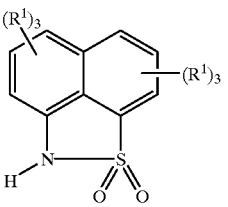

wherein $R^1$ is as previously defined, to produce a compound of formula 4'.

In particular, processes of interest are those described above wherein P represents a member selected from the group consisting of: TES, TMS, TBDMS, PNB, p-nitrobenzyloxycarbonyl, allyl and allyloxycarbonyl.

Other processes that are of particular interest are those described above wherein P* represents a member selected from the group consisting of: TES, TMS, TBDMS, PNB, and allyl.

Still other processes that are of particular interest are those described above wherein R represents methyl.

Still other processes that are of particular interest are those described above wherein $R^3$ represents I.

Still other processes that are of particular interest are those described above wherein $R^3$ represents Cl.

Still other processes that are of particular interest are those described above wherein L represents a leaving group selected from the group consisting of: diphenylphosphoryl, halo, mesyl and triflate.

Compounds which are of interest herein include those represented by one of the following formulas:

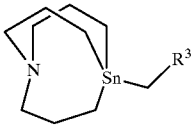

wherein $R^3$ is Cl, Br or I;

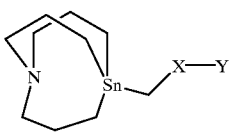

wherein
X represents O or NH and Y represents H or a protecting group, or X and Y taken in combination represent a ring system containing from 0–3 nitrogen atoms and 0–2 heteroatoms selected from O, S, S(O) and S(O)$_2$, said ring system having 1–4 rings, with from 5–16 atoms, said system being non-aromatic, partially aromatic or aromatic, and being unsubstituted or substituted with from 1–3 groups selected from halo, OH, OP, wherein P is a protecting group, C$_{1-6}$ alkyl and C$_{1-6}$ alkyl substituted with from 1–3 of halo, OH, OP, NH$_2$, NHC$_{1-4}$ alkyl and N(C$_{1-4}$ alkyl)$_2$

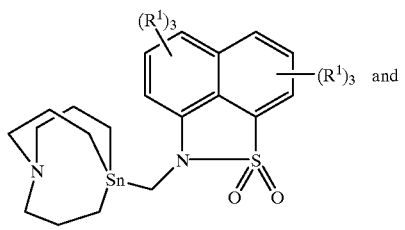

wherein each R$^1$ represents H, halo, OH, OP wherein P is a protecting group, C$_{1-6}$ alkyl or C$_{1-6}$ alkyl substituted with 1–3 of halo, OH, OP, NH$_2$, NHC$_{1-4}$ alkyl or N(C$_{1-4}$ alkyl)$_2$.

Species that are of particular interest are as follows:

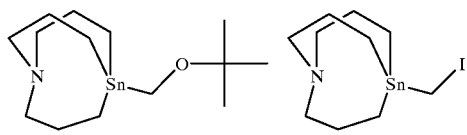

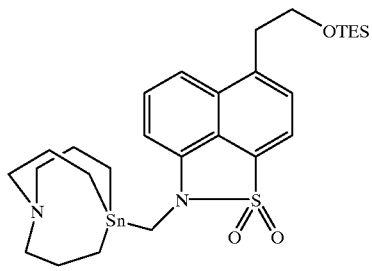

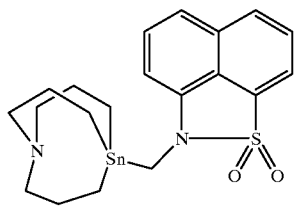

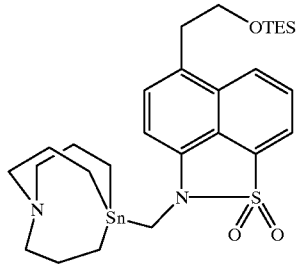

-continued

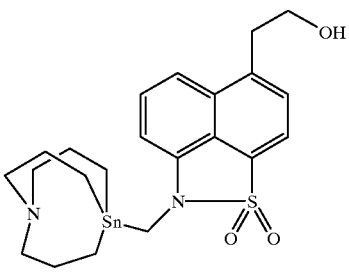

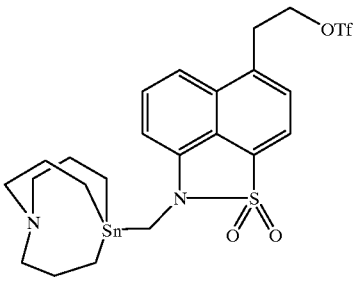

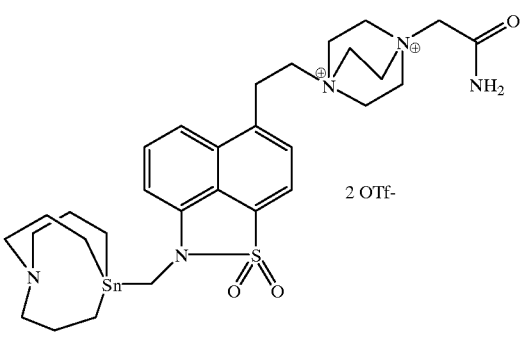

and

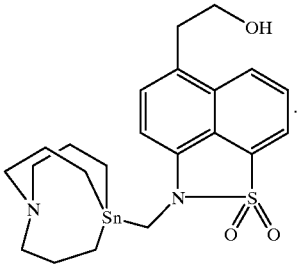

The process of the present invention is illustrated by the following generic scheme:

FLOW SHEET A

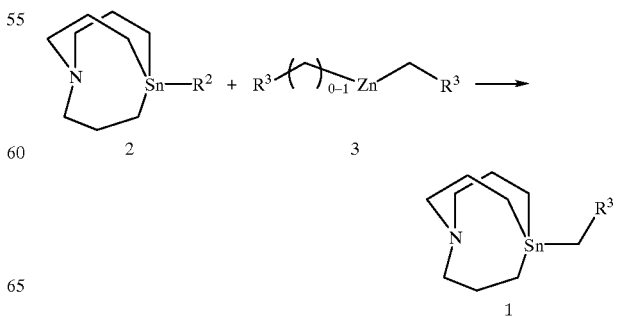

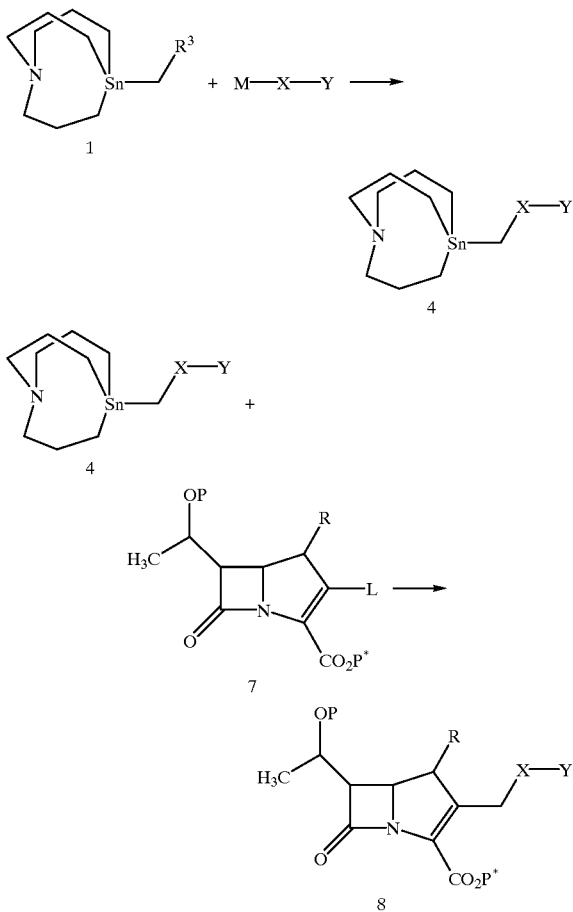

Alternatively 4 can be prepared by treatment of the halostannatrane 2 with MCHXY in a solvent such as THF, t-butyl methyl ether and the like at about −100° C. to about 35° C. followed by an appropriate workup and isolation, wherein X=O and Y=tertiary butyl.

Addition of the CH$_2$XY moiety to the carbapenem is accomplished by cross-coupling suitably protected 7 with stannatrane 4 in a suitable solvent such as dimethylpropylene urea (DMPU), hexamethylphosphoramide (HMPA), THF, toluene, DMF, NMP, NEP, and the like using an appropriate transition metal catalyst such as Pd(dba)$_2$ and a ligand such as triphenyl phosphine, tris-2-furyl phosphine, triphenyl arsine and the like. The temperature for this reaction is typically between 20° C. and 100° C. and the products are isolated by common techniques such as chromatography or crystallization.

Suitable solvents for the invention disclosed herein include tetrahydrofuran (THF), ethyl acetate (EtOAc), H$_2$O, C$_{1-6}$ alcohol, toluene, DMF, NMP, NEP, dichloromethane, acetonitrile, acetone and the like The synthesis of the target intermediate is completed by removing any protecting groups which are present in the penultimate intermediate 6. The deprotected final product is then purified, as necessary, using techniques such as ion exchange chromatography, HPLC on reverse phase silica gel, MPLC on reverse phase polystyrene resin and recrystallization.

The final product may be characterized structurally by techniques such as NMR, IR, MS, and UV. For ease of handling, the final product, if not crystalline, may be lyophilized from water to afford an amorphous, easily handled solid.

Still another aspect of the process that is of interest is the synthesis of a carbapenem compound of formula 6:

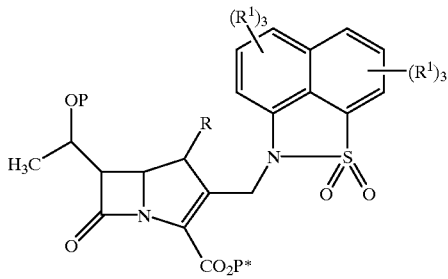

wherein R represents H or methyl, P and P* represent protecting groups and each R$^1$ is as described above, comprising reacting a compound of formula 4':

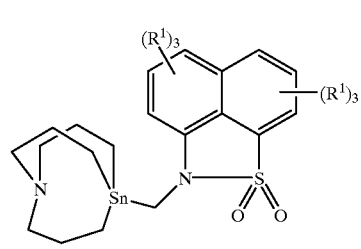

The stannatrane 2 having a halo group attached directly to the tin atom can be obtained in accordance with Vedejs, E. et al. J. Am. Chem. Soc. 114: 6556–6558 (1992), the teachings of which are incorporated herein by reference. The carbapenem 7 having a leaving group at position 2 can likewise be obtained in accordance with Schmitt, S. M. et al., J. Antibiotics 41(6): 780–787 (1988), the teachings of which are incorporated herein by reference. The carboxylic acid group at C-3 of the carbapenem is generally protected as a carboxyl protecting group such as p-nitrobenzyl (PNB), allyl, p-methoxybenzyl, trichloroethyl, 2-trimethylsilylethyl, and the like. Furthermore, the hydroxyl group of the 6-(hydroxyethyl) side-chain is optionally protected with a hydroxyl protecting group such as trimethylsilyl (TMS), triethylsilyl (TES), tert-butyldimethylsilyl (TBDMS), tert-butyldiphenylsilyl (TBDPS), acetyl, allyloxycarbonyl, 2-trimethylsilylethoxy carbonyl, 2-trichloroethoxycarbonyl and the like.

The compounds of the present invention are prepared as illustrated in flow sheet A. Treatment of stannatrane 2 with halomethyl zinc halide or bis halomethyl zinc reagents 3 in a suitable solvent such as tetrahydrofuran (THF) at about −78° C. to about 35° C. for about 1 to 20 hours followed by isolation techniques yields the halomethyl stannatrane 1.

Reaction of 1 in a suitable solvent such as THF, DMF, DMSO, and the like with organometallic reagent MXY yields 4 which can be isolated by chromatography or crystallization.

with a compound of formula 9:

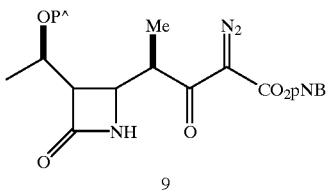

wherein R, P and P* are as previously defined, P◯ represents a protecting group or hydrogen and L represents a leaving group, in the presence of a catalyst (such as rhodium octanoate, rhodium acetate and the like), and metal halide (such as zinc bromide, zinc chloride, and the like) contacting the mixture with a base (such as $C_{1-6}$ alkylamines such as diisopropyl amine, t-butyl amine, 2,2,6,6,tetramethylpiperidine, methylamine, hexylamine, ethylamine, triethylamine, diisopropylethylamine, trimethylamine, ethyldimethylamine, tri-n-propylamine and the like, 1,8-diazabicyclo[5.4.0]undec-7-ene (DBU), pyridine, imidazole, lutidine, collidine, 4-dimethylaminomethyl-pyridine, N,N,N',N'-tetramethylethylenediamine (TMEDA), N-methylmorpholine (NMM) and the like) and triflating agent (such as trifluoromethanesulfonic anhydride and the like) and reacting the resulting solution with a palladium catalyst (such as $Pd(OAc)_2$, $Pd(PPh_3)_4 PdCl_2$, $PdCl_2(PPh_3)_2$, $PdCl_2(CH_3CN)_2$, $Pd_2(dba)_3$, $Pd_2(dba)_3 CHCl_3$, $Pd(dba)_2$, and the like, wherein dba is dibenzylideneacetone) in the presence of a ligand (such as a ligand such as triphenyl phosphine, tris-2-furyl phosphine, triphenyl arsine and the like) to produce a compound of formula 6.

The compounds of the present invention are valuable intermediates for antibacterial agents that are active against various Gram-positive and to a lesser extent Gram-negative bacteria, and accordingly find utility in human and veterinary medicine.

Many of the compounds that can be made in accordance with the present invention are biologically active against MRSA/MRCNS. In vitro antibacterial activity is predictive of in vivo activity when the compounds are administered to a mammal infected with a susceptible bacterial organism.

Using standard susceptibility tests, the compounds of the invention are determined to be active against MRSA.

The compounds of the invention can be formulated in pharmaceutical compositions by combining the compound with a pharmaceutically acceptable carrier. Examples of such carriers are set forth below.

The invention is further described in connection with the following non-limiting examples.

Preparative Example 1

SYNTHESIS OF 4-(2-(TRIMETHYLSILYLOXY)-ETHYL)-1,8-NAPHTHOSULTAM

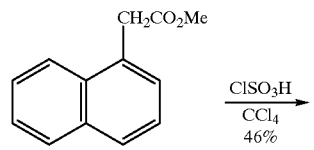

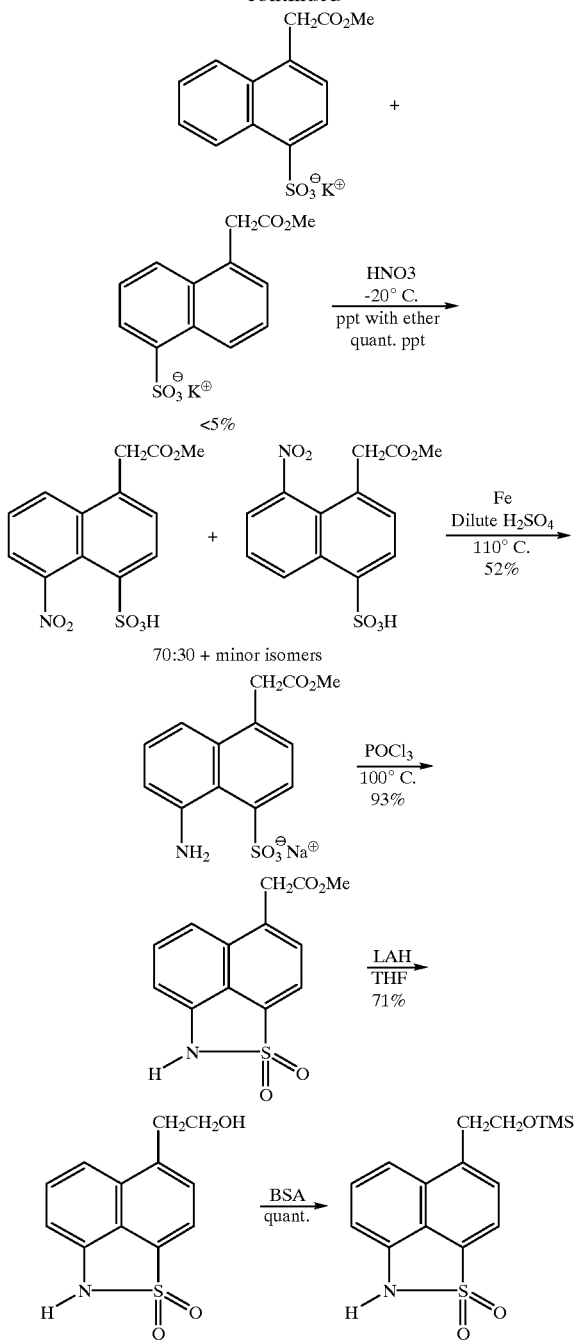

Step 1 potassium 1-(methoxycarbonylmethyl)-4-naphthalene sulfonate

A solution of methyl 1-naphthaleneacetate (1 mL, 5.77 mmol) in carbon tetrachloride (1 mL) was cooled under nitrogen in an ice bath. Chlorosulfonic acid (0.38 mL, 5.7 mmol) was added dropwise over 8 minutes. After an additional 30 minutes, the viscous mixture was removed from the bath and was stirred at room temperature for 17 hours to give a white solid. The solid was partitioned between methylene chloride (5 mL) and water (5 mL). After filtering through solka-floc, the methylene chloride layer was extracted with more water (2×5 mL), and the combined aqueous extracts were basified with potassium carbonate to give a precipitate. The suspension was concentrated to approximately 5 mL and was cooled in an ice bath.

The suspension was then filtered and the collected solid was washed with cold water (2 mL). The solid was dried under a stream of nitrogen to give the title compound as a white solid (0.84 g).

$^1$H NMR (DMSO-d$_6$, 500 MHz) δ3.73 (s, OMe), 4.27 (s, CH$_2$Ar), 7.53 (d, ArH), 7.71 (t, ArH), 7.76 (t, ArH), 8.06 (d, ArH), 8.10 (d, ArH) and 8.73 (d, ArH).

Step 2

1-(methoxycarbonylmethyl)-5-nitro-4-naphthalene sulfonic acid

Potassium 1-(methoxycarbonylmethyl)-4-naphthalene sulfonate (10 g, 31.4 mmol) was added portionwise over 30 minutes to 90% nitric acid, which was cooled in a methanol/ice bath to approximately −15° C. After 2 hours, the bath temperature had reached −10° C. and diethyl ether (200 mL) was added to the mixture. The precipitated solid was filtered, washed with ether (100 mL) and isopropanol (20 mL), and dried under a stream of nitrogen to give the title compound as an approximately 70:30 mixture of the 5- and 8-nitro isomers (approximately 12 g).

$^1$H NMR (D$_2$O, 500 MHz) δ3.69 (s, OMe), 4.30 (s, CH$_2$Ar), 7.67 (t, ArH), 7.71 (d, ArH), 8.18 (d, ArH), 8.29 (d, ArH) and 8.33 (d, ArH).

Step 3 sodium 1-(methoxycarbonylmethyl)-5-amino-4-naphthalene sulfonate 1-(methoxycarbonylmethyl)-5-nitro-4-naphthalene sulfonic acid (2 g, 6.15 mmol) was dissolved in water (20 mL), containing 0.5 mL concentrated sulfuric acid, and was added dropwise over 5 minutes to a refluxing suspension of iron (4 g, 71.6 mmol) in water (100 mL). After refluxing for one hour, the dark mixture was cooled to room temperature, made basic with sodium carbonate, and concentrated to approximately 30 mL. The residual mixture was placed on a CG-161 AMBERCHROM resin column (2.5×30 cm). The column was washed with water (200 mL), 10% MeCN/H$_2$O (200 mL), and 25% MeCN/H$_2$O (400 mL), collecting 25 mL fractions. Fractions 21–28 were combined and evaporated to give the title compound as a dark solid (0.675 g).

$^1$H NMR (D$_2$O, 500 MHz) δ3.64 (s, OMe), 4.18 (s, CH$_2$Ar), 7.04 (d, ArH), 7.38 (d, ArH), 7.41 (d, ArH), 7.45 (t, ArH) and 8.22 (d, ArH).

Step 4

4-(methoxycarbonylmethyl)-1,8-naphthosultam

Sodium 1-(methoxycarbonylmethyl)-5-amino-4-naphthalene sulfonate (0.675 g, 2.13 mmol) was suspended in phosphorous oxychloride (10 g, 65.2 mmol) and was refluxed for 1 hour to give a thin suspension. The mixture was cooled to room temperature and was partitioned between ethyl acetate (100 mL) and water (100 mL). The water layer was extracted with ethyl acetate (50 mL) and the combined ethyl acetate layers were washed with saturated aqueous sodium chloride (100 mL), dried over magnesium sulfate, filtered and evaporated to give the title compound as a solid (0.55 g).

$^1$H NMR (CDCl$_3$, 500 MHz) δ3.72 (s, OMe), 4.15 (s, CH$_2$Ar), 6.86 (br s, NH), 6.97 (d, ArH), 7.60 (t, ArH), 7.67 (d, ArH), 7.71 (d, ArH) and 7.95 (d, ArH).

Step 5

4-(2-(hydroxy)-ethyl)-1,8-naphthosultam

A solution of 4-(methoxycarbonylmethyl)-1,8-naphthosultam (0.2 g, 0.72 mmol) in tetrahydrofuran (2 mL) was cooled under nitrogen in an ice bath. Lithium aluminum hydride (1.44 mL of a 1.0 M solution in THF, 1.44 mmol) was added over 1 minute to give a light yellow suspension. After 30 minutes, water was carefully added and the mixture was partitioned between ethyl acetate (30 mL) and 1N hydrochloric acid (10 mL). The aqueous layer was extracted with ethyl acetate (50 mL) and the combined ethyl acetate layers were washed with saturated aqueous sodium chloride (10 mL), dried over magnesium sulfate, filtered and evaporated. The residual solid (0.16 g) was purified by preparative thin layer chromatography (2×1000 micron silica gel plates, developed/eluted with 5% MeOH/CH$_2$Cl$_2$) to give the title compound as a solid (0.127 g).

$^1$H NMR (0.14 mL CDCl$_3$ and 0.01 mL CD$_3$OD, 500 MHz) δ3.33 (t, CH$_2$Ar), 3.91 (t, CH$_2$OH), 6.84 (d, ArH), 7.49 (dd, ArH), 7.59 (d, ArH), 7.59 (d, ArH) and 7.83 (d, ArH).

Step 6

4-(2-(trimethylsilyloxy)-ethyl)-1,8-naphthosultam

N,O-Bistrimethylsilylacetamide (0.31 mL, 1.25 mmol) was added to a solution of 4-(2-(hydroxy)-ethyl)-1,8-naphthosultam (0.125 g, 0.50 mmol) in tetrahydrofuran (1 mL). After one hour the mixture was evaporated and the residue was dissolved in methylene chloride (2 mL) and filtered through silica gel (2.5 g). The silica gel was eluted with methylene chloride (50 mL), the solvent was evaporated and the residue was lyophilized from benzene (3 mL) to give the title compound as an oil (0.16 g, quant.).

$^1$H NMR (CDCl$_3$, 500 MHz) δ0.035 (s, TMS), 3.37 (t, CH$_2$Ar), 3.94 (t, CH$_2$O(TMS)), 6.95 (d, ArH), 7.56 (dd, ArH), 7.64 (d, ArH), 7.71 (d, ArH) and 7.92 (d, ArH).

EXAMPLE 1

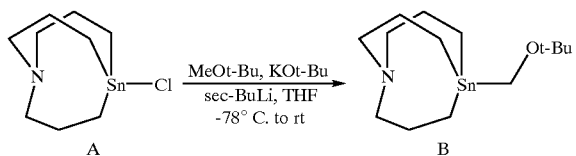

A stirred suspension of potassium t-butoxide (1.68 g, 15.0 mmol) and t-butylmethyl ether (54 mL) under an atmosphere of dry nitrogen was cooled to −78° C. A solution of sec-BuLi (9.1 mL of a 1.65 M solution in cyclohexane, 15.0 mmol) was added to the suspension over 5 min. After 2 h at −78° C., a solution of 1-aza-5-chloro-5-stannabicyclo[3.3.3] undecane (A, 2.93 g, 10.0 mmol) and THF (60 mL) was added and the mixture was allowed to warm to rt over 4 h. After an additional 16 h at rt the solution was poured onto water (100 mL) and hexane (300 mL). The layers were partitioned and the organic phase was washed with water (2×100 mL), brine (50 mL) and dried (MgSO$_4$) then concentrated to provide B as a clear light yellow oil (2.82 g).

$^1$H NMR (CDCl$_3$, 250 MHz) δ3.09 (t, J=6.4 Hz, 2H), 2.34 (m, 6H), 1.62 (m, 6H), 1.06 (s, 9H), 0.68 (m, 6H), $^{13}$C NMR (CDCl$_3$, 63 MHz) δ72.9, 56.2, 54.7, 26.8, 23.2, 5.7.

EXAMPLE 2

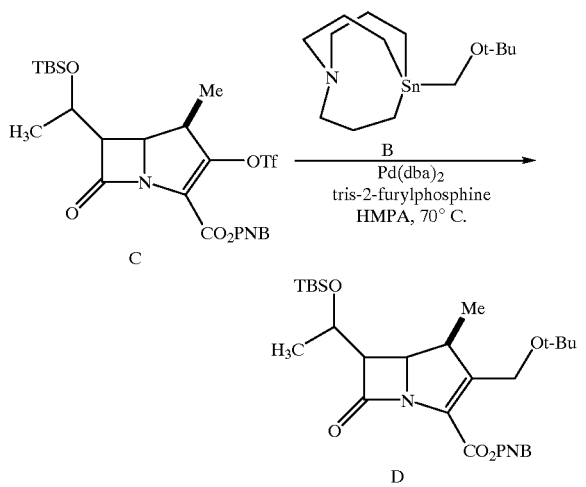

A solution of Pd(dba)₂ (19 mg, 0.03 mmol), tris-2-furylphosphine (19 mg, 0.08 mmol) and HMPA (1 mL) was heated to 50° C. under a nitrogen atmosphere for 15 min. To the resulting yellow solution was added a solution of enol triflate (C, 201 mg, 0.33 mmol), of 1-aza-5-t-butoxymethyl-5-stannabicyclo[3.3.3]undecane (B, 173 mg, 0.50 mmol) and HMPA (1 mL) via cannula. The resulting solution was aged at 70° C. for 2 h. The mixture was diluted with t-butylmethyl ether (50 mL) and then washed with water (3×10 mL). The organic phase was dried (MgSO₄) and concentrated to provide a brown oil (318 mg). Flash chromatography on silica gel with 95:5 hexane/EtOAc eluent provided D as a colorless crystalline solid (110 mg, 61%).

$^1$H NMR (CDCl₃, 250 MHz) δ8.19 (m, 2H), 7.64 (m, 2H), 5.43 (d, J=13.9 Hz, 1H), 5.21 (d, J=13.9 Hz, 1H), 4.80 (d, J=14.1 Hz, 1H), 4.23 (m, 2H), 4.03 (dd, J=14.2, 1.0 Hz, 1H), 3.40 (m, 1H), 3.22 (dd, J=5.7, 3.0 Hz, 1H), 1.23 (d, J=6.2 Hz, 3H), 1.20 (s, 9H), 1.15 (d, J=7.5 Hz, 3H), 0.84 (s, 9H), 0.58 (s, 3H), 0.52 (s, 3H), $^{13}$C NMR (CDCl₃, 63 MHz) δ175.2, 160.8, 152.6, 147.5, 142.9, 127.9, 125.5, 123.6, 73.5, 65.8, 65.1, 60.1, 56.4, 55.6, 40.1, 27.3, 25.6, 22.3, 17.8, 15.3, −4.3,−5.1.

EXAMPLE 3

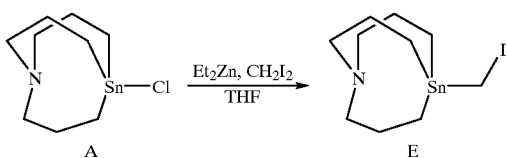

Diethyl zinc (0.4 mL, 3.9 mmol) was added to dry THF (5 mL) under nitrogen at −70° C. Diiodomethane (0.6 mL, 7.4 mmol) was added dropwise. The mixture was aged at 0° C. for 1 h and then 30 min at 23° C. The solution was cooled to 0° C. and 1-aza-5-chloro-5-5 stannabicyclo[3.3.3] undecane (A, 450 mg, 1.5 mmol) was added in one portion. The mixture was stirred at rt for 20 h. Diethyl ether (10 mL) and water (10 mL) were added and the layers were partitioned. The organic phase was concentrated and the residue was applied to a silica column. Elution with hexane/EtOAc provided 1-aza-5-iodomethyl-5-stannabicyclo[3.3.3] undecane (E) as a white solid (500 mg).

$^1$H NMR (CDCl₃, 250 MHz) δ2.37 (m, 6H), 1.67 (m, 6H), 1.66 (s, 2H), 0.82, (m, 6H). $^{13}$C NMR (CDCl₃, 63 MHz) δ54.6, 23.3, 7.2, −13.5.

EXAMPLE 4

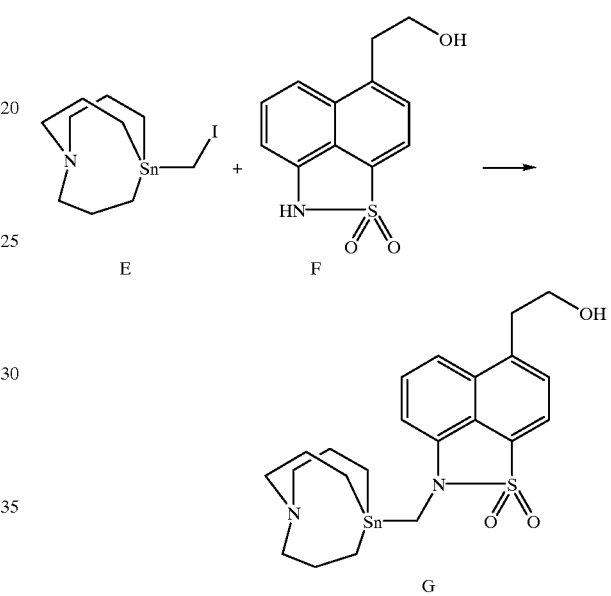

A suspension of 1-aza-5-iodomethyl-5-stannabicyclo [3.3.3]undecane (E, 100 mg, 0.25 mmol), hydroxyethyl-naphthosultam (F, 81 mg, 0.33 mmol), K₂CO₃ (45 mg, 0.33 mmol) and DMF (0.5 mL) was stirred at 23° C. for 10 h. The mixture was partitioned between ether (5 mL) and water (5 mL) and the organic phase was washed with water (5 mL), dried (MgSO₄) then concentrated. The compound G was isolated by chromatography on silica with 4:1 hexane/ EtOAc eluent to provide a white solid (110 mg).

$^1$H NMR (CDCl₃, 250 MHz) δ7.81 (d, J=7.4 Hz, 1H), 7.44 (m, 3H), 6.52 (m, 1H). 3.91 (br m, 2H), 3.29 (t, J=6.6 Hz, 2H), 2.90 (m, 2H). 2.35 (m, 6H), 1.65 (m, 6H), 0.82 (m, 6H), $^{13}$C NMR (CDCl₃, 63 MHz) δ140.7, 138.8, 129.6, 129.4, 129.2, 128.4, 119.6, 119.3, 113.7, 102.1, 62.8, 54.7, 35.8, 29.8, 23.2, 8.1.

EXAMPLE 5

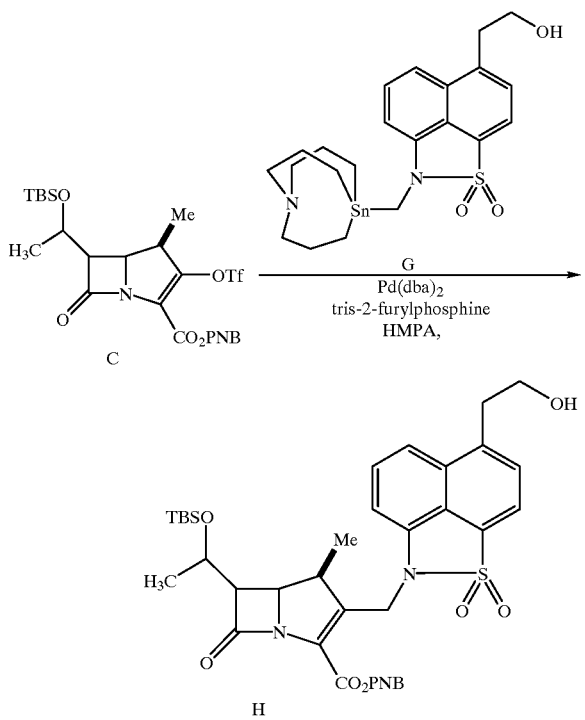

A solution of Pd(dba)$_2$ (19 mg, 0.03 mmol), tris-2-furylphosphine (19 mg, 0.08 mmol) and HMPA (0.7 mL) was heated to 50° C. under a nitrogen atmosphere for 30 min. The resulting yellow solution was added to a solution of enol triflate C (167 mg, 0.27 mmol), stannane G (110 mg, 0.21 mmol) and HMPA (0.7 mL) via cannula. The resulting solution was warmed to 75° C. for 3 h then cooled to room temperature. The mixture was diluted with ether (10 mL) and then washed with water (10 mL). The organic phase was dried (MgSO$_4$) and concentrated. The compound H was isolated by preparative TLC using hexane/EtOAc as eluent to provide a colorless solid (78 mg).

$^1$H NMR (CDCl$_3$, 250 MHz) δ8.24 (m, 2H), 7.93 (m, 1H), 7.73–7.47 (m, 5H), 6.72 (d, J=7.2 Hz, 1H), 5.54 (d, J=13.9 Hz, 1H), 5.40 (d, J=17.2 Hz, 1H), 5.37 (d, J=13.96 Hz, 1H), 4.66 (d, J =17.2 Hz, 1H), 4.24 (m, 2H), 4.01 (t, J=6.5 Hz, 2H), 3.38 (m, 3H), 3.30 (dd, J=4.9, 3.0 Hz, 1H), 1.29 (d, J=7.3 Hz, 3H), 1.20 (d, J=6.2 Hz, 3H), 0.83 (s, 9H), 0.06 (s, 3H), 0.05 (s, 3H), $^{13}$CNMR (CDCl$_3$, 63 MHz) δ174.5, 161.1, 147.7, 147.1, 142.5, 141.6, 137.2, 129.9, 129.3, 129.0, 128.9, 128.3, 128.2, 123.8, 120.0, 119.7, 115.9, 103.8, 65.7, 65.4, 62.9, 60.4, 55.4, 40.7, 38.0, 35.7, 25.7, 22.2, 17.9, 15.6, −4.3, −5.0

EXAMPLE 6

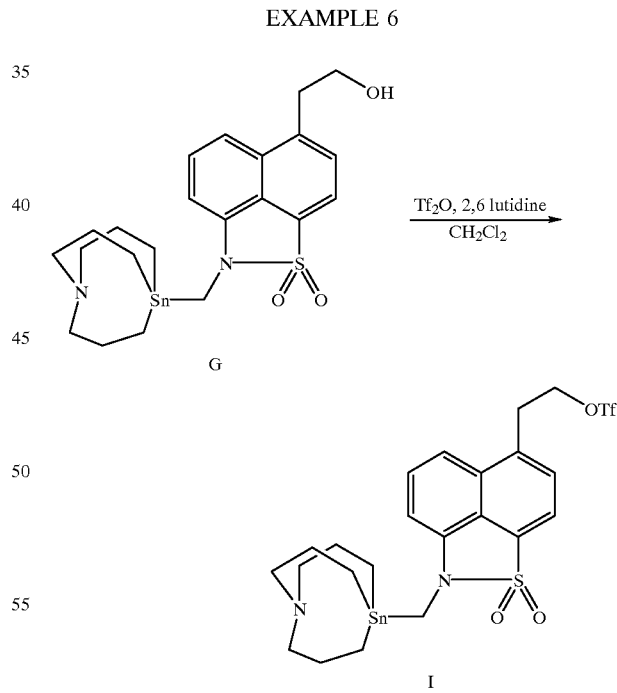

A solution of alcohol G (521 mg, 1.0 mmol) and methylene chloride (10 mL) was cooled to −78° C. under nitrogen and 2,6-lutidine (0.26 mL, 2.2 mmol) was added dropwise. After 10 min, trifluoromethanesulfonic anhydride (0.18 mL, 1.1 mmol) was added dropwise and the solution was warmed to −20° C. over 2 h. The reaction mixture was applied to a 1.2 cm pad of silica that was eluted with methylene chloride.

The solvent was removed in vacuo to provide I as a yellow solid (571 mg, 87%).

¹H NMR (CDCl₃, 250 MHz) δ7.82 (d, J=7.4 Hz, 1H), 7.55 (m, 2H), 7.34 (d, J=8.6 Hz, 1H), 6.56 (d, J=7.3 Hz, 1H), 4.78 (t, J=7.1 Hz, 2H), 3.58 (t, J=7.1 Hz, 2H), 2.91 (t, J=5.5 Hz, 2H), 2.36 (t, J=5.5 Hz, 6H), 1.65 (m, 6H), 0.82 (m, 6H). ¹³C NMR (CDCl₃, 62.9 MHz) δ138.9, 136.0, 130.2, 129.2, 128.8, 119.5, 119.1, 118.4 (q, J=320 Hz), 112.5, 102.3, 75.6, 54.5, 32.3, 29.8, 23.0, 8.0.

¹H NMR (CD₃CN, 250 MHz) δ7.98 (d, J=7.5 Hz, 1H), 7.73 (d, J=7.5 Hz, 1H), 7.60 (m, 1H), 7.50 (d, J=8.7 Hz, 1H), 6.83 (b, 1H), 6.69 (d, J=7.3 Hz, 1H), 6.43 (b, 1H), 4.22 (s, 2H), 4.15 (m, 6H), 3.97 (m, 6H), 3.80 (m, 2H), 3.60 (m, 2H), 2.92 (s, 2H), 2.37 (t, J=5.6 Hz, 6H), 1.63 (m, 6H), 0.74 (t, J=6.8 Hz, 6H).

EXAMPLE 7

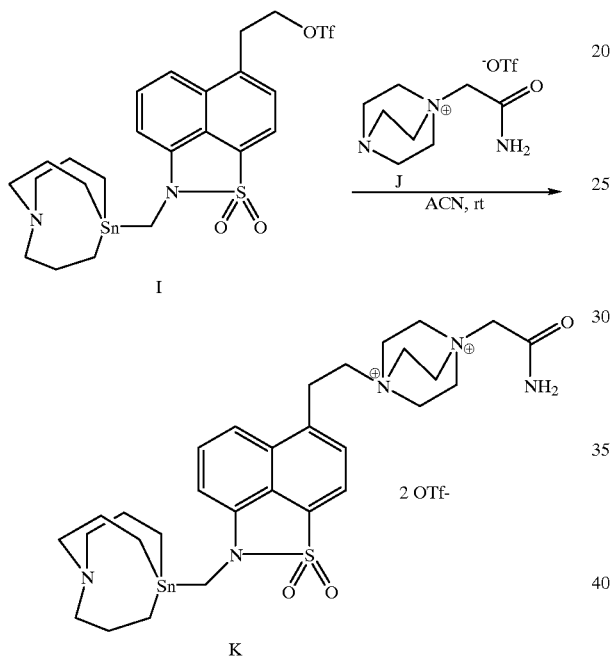

A solution of triflate I (2.89 g, 4.42 mmol) and acetonitrile (40 mL) was cooled under nitrogen to −10° C. and dabcoacetamide triflate J (1.49 g, 4.87 mmol) was added in one portion. The resulting mixture was stirred at rt for 18 h. The reaction mixture was added slowly to rapidly stirred diethylether (200 mL) and compound K was collected on a frit to provide 4.17 g of a yellow solid that was 93 wt % pure (90.3% yield, corrected).

EXAMPLE 8

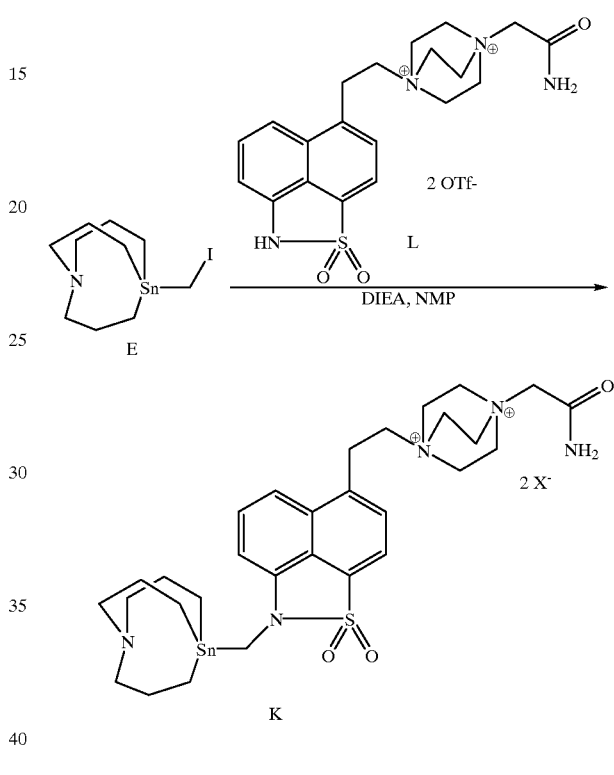

Iodomethylstannatrane E (1.01 g, 2.53 mmol), naphthosultam L (1.78 g, 2.53 mmol), diisopropylethylamine (1.32 mL, 7.29 mmol) and N-methylpyrolidinone (30 mL) were combined and stirred at rt for 18 h. HPLC assay shows 91% assay yield. The reaction mixture was added slowly to rapidly stirred diethyl ether (300 mL). The resulting yellow solid K was collected on a frit (3.17 g, 51 wt %, 65% isolated yield). A pure sample was obtained by chromatography on C18 silica eluting with 20% to 40% acetonitrile and water. X represents the counterions for K, which is a mixture of iodide and triflate.

EXAMPLE 9

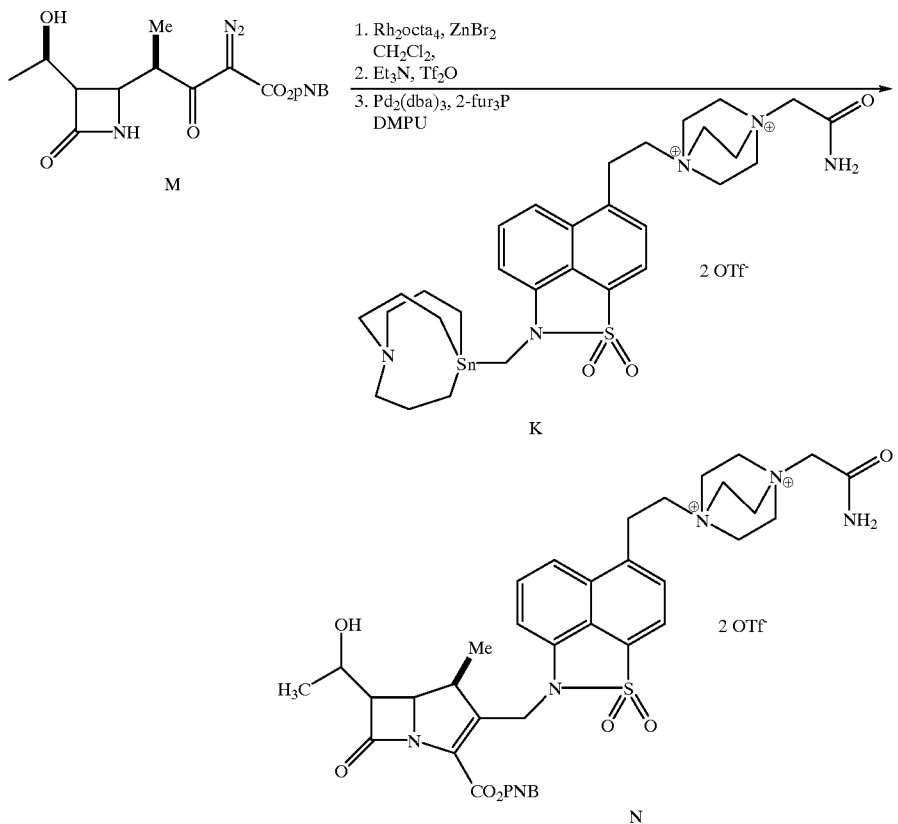

A mixture of diazoketone M (2.00 g), Rh$_2$(octa)$_4$ (19.9 mg), ZnBr$_2$ (11.8 mg) and CH$_2$Cl$_2$ (20 mL) was refluxed for 4 h. The mixture was cooled to −78° C. and triethylamine (0.65 mL) was added dropwise. After 30 min Tf$_2$O (0.87 mL) was added dropwise. After an additional 30 min DMPU (20 mL) was added and the mixture was warmed to 24° C.

A separate flask was charged with Pd$_2$(dba)$_3$–CHCl$_3$ (20.7 mg), 2-fur$_3$P (23.2 mg) and DMPU (1 mL). The mixture was degassed then warmed to 70° C. for 30 min to provide a clear yellow solution.

A separate flask was charged with the stannane K coupling partner (200 mg), the enol triflate solution (2.69 mL of a 0.115 M solution) and the catalyst solution. The mixture was degassed then warmed to 70° C. After 2 h the assay yield of N was 47%.

EXAMPLE 10

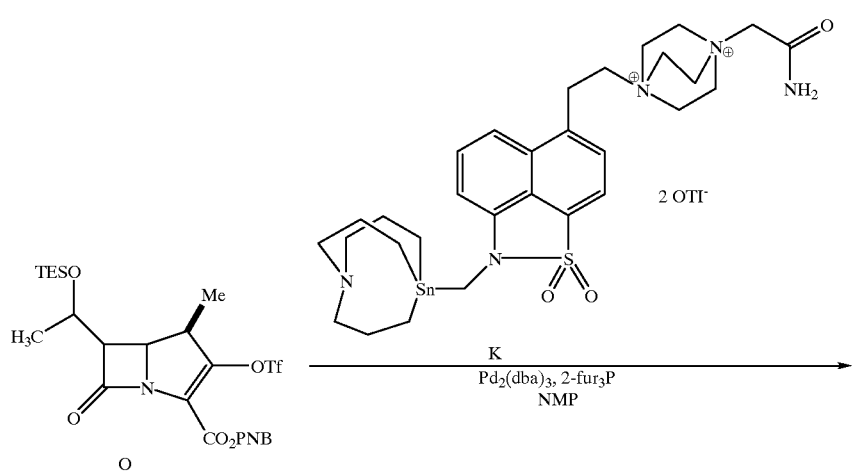

-continued

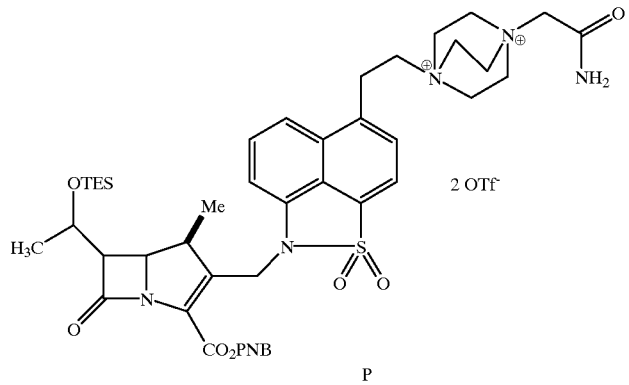

P

Pd$_2$(dba)$_3$–CHCl$_3$ (31.6 mg,) 2-fur$_3$P (35.4 mg) and NMP (2 mL) were combined, degassed with N$_2$ and warmed to 60° C. for 30 min.

The enol triflate (743 mg), stannatrane K (972 mg), diisopropylethylamine (47 mg) and NMP were combined, degassed with N$_2$ and warmed to 60° C. After 3 h the assay yield of P was 98.5% based on the current standard. The crude reaction mixture was diluted with THF (50 mL) and the resulting mixture was washed with 20% aqueous NaCl (3×50 mL). The THF was removed in vacuo and the residue was diluted with acetonitrile (5 mL). The resulting suspension was filtered through a frit providing 179 mg of crystalline stannatrane chloride A. To the mother liquor was added dropwise isopropanol (20 mL) and the resulting solid coupling product P (1.243 g) was collected on a frit. The mother liquor was concentrated to dryness then triturated with methanol (2 mL). The remaining solid stannatrane chloride A (116 mg) was collected on a frit.

EXAMPLE 11

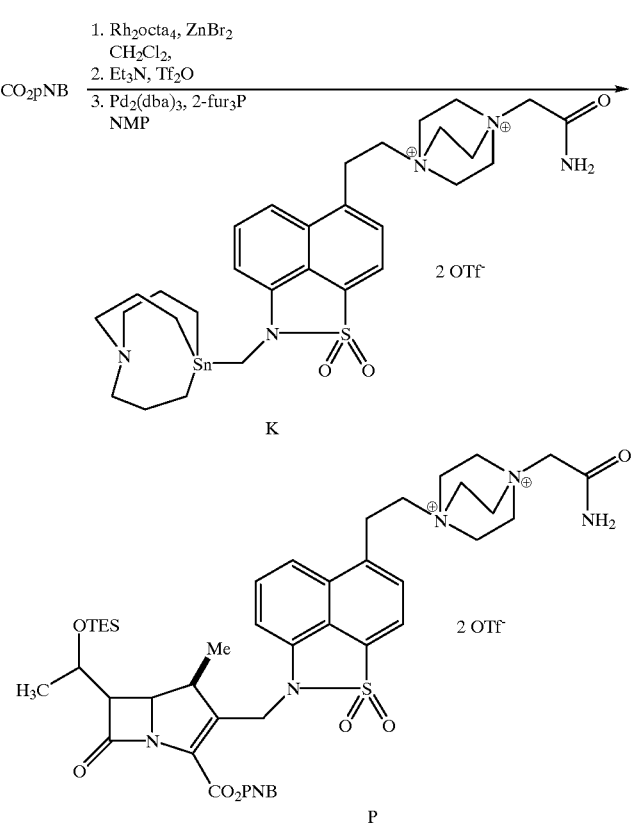

A mixture of diazoketone Q (2.02 g), Rh$_2$(octa)$_4$ (16 mg), ZnBr$_2$ (49 mg) and CH$_2$Cl$_2$ (10 mL) was refluxed for 3 h. The mixture was cooled to −72° C. and triethylamine (0.72 mL) was added dropwise. After 30 min Tf$_2$O (0.71 mL) was added dropwise. After an additional 30 mn NMP (12 mL) was added and the mixture was warmed to 24° C. The methylene chloride was removed in vacuo.

A separate flask was charged with Pd$_2$(dba)$_3$-CHCl$_3$ (2.6 mg), 2-fur$_3$P (2.9 mg) and NMP (0.25 mL). The mixture was degassed with $N_2$ then warmed to 70° C. for 30 min to provide a clear yellow solution.

A separate flask was charged with the stannane K (97 mg), the enol triflate solution (0.42 mL of the 0.29 M solution), diisopropylethyl-amine (3.9 mg), NMP (1.24 mL), and the catalyst solution. The mixture was degassed then warmed to 70° C. After 6 h the assay yield of P was 70%.

What is claimed is:

1. A process of synthesizing a carbapenem compound of formula 6:

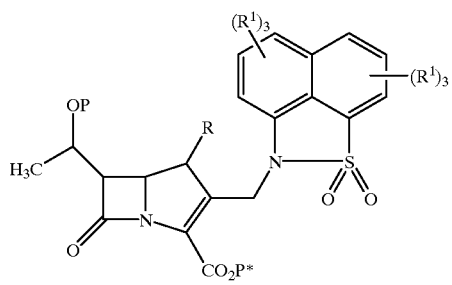

6 wherein
R represents H or methyl, P and P* represent protecting groups and each $R^1$ represents H, halo, OH, OP wherein P is a protecting group, —$C_{1-6}$ straight- or branched-chain alkyl, unsubstituted or substituted with one to four $R^d$ groups; and —$C_{3-7}$ cycloalkyl, unsubstituted or substituted with one to four $R^d$ groups;

each $R^d$ independently represents halo; OP, wherein P is a protecting group, —CN; —$NO_2$; —$NR^eR^f$; —$OR^g$; —$SR^g$; —$CONR^eR^f$; —$COOR^g$; —$SOR^g$; —$SO_2R^g$; —$SO_2NR^eR^f$; —$NR^eSO_2R^f$; —$COR^e$; —$NR^eCOR^f$; —$OCOR^e$; —$OCONR^eR^f$; —$NR^eCONR^fR^g$; —$NR^eCO_2R^h$; —$OCO_2R^h$; —$C(NR^e)NR^fR^g$; —$NR^eC(NH)NR^fR^g$; —$NR^eC(NR^f)R^g$; —R* or —Q;

$R^e$, $R^f$ and $R^g$ represent hydrogen; —R*; —$C_{1-6}$ straight- or branched-chain alkyl unsubstituted or substituted with one to four $R^i$ groups;

each $R^i$ independently represents halo; —CN; —$NO_2$; phenyl; —$NHSO_2R^h$; —$OR^h$; —$SR^h$; —$N(R^h)_2$; —$N^+(R^h)_3$; —$C(O)N(R^h)_2$; —$SO_2N(R^h)_2$; heteroaryl; heteroarylium; —$CO_2R^h$; —$C(O)R^h$; —$OCOR^h$; —$NHCOR^h$; guanidinyl; carbamimidoyl or ureido;

each $R^h$ independently represents hydrogen, a —$C_{1-6}$ straight or branched-chain alkyl group, a —$C_3$–$C_6$ cycloalkyl group or Q is selected from the group consisting of wherein R* and Q are balanced by the maximum positive charges represented by R* and/or Q is two and negatively charged counterions:

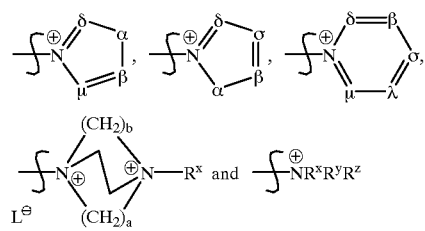

wherein:
a and b are 1, 2 or 3;
$L^-$ is a pharmaceutically acceptable counterion;
α represents O, S or $NR^s$;
β, δ, λ, μ and σ represent $CR^t$, N or $N^+R^s$, provided that no more than one of β, δ, λ, μ and σ is $N^+R^s$;
R* is selected from the group consisting of:

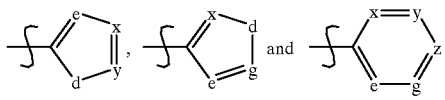

wherein:
the maximum positive charges represented by R* and/or Q is two and
d represents O, S or $NR^k$;
e, g, x, y and z represent $CR^m$, N or $N^+R^k$, provided that no more than one of e, g, x, y and z in any given structure represents $N^+R^k$;

$R^k$ represents hydrogen; —$C_{1-6}$ straight- or branched-chain alkyl, unsubstituted or substituted with one to four $R^i$ groups; or —$(CH_2)_nQ$ where n=1, 2 or 3 and Q is as previously defined;

each $R^m$ independently represents a member selected from the group consisting of: hydrogen; halo; —CN; —$NO_2$; —$NR''R^o$; —$OR''$; —$SR''$; —$CONR''R^o$; —$COOR^h$; —$SOR''$; —$SO_2R''$; —$SO_2NR_nR^o$; —$NR''SO_2R^o$; —$COR''$; —$NR''COR^o$; —$OCOR''$; —$OCONR''R^o$; —$NR''CO_2R^h$; —$NR''CONR^oR^h$; —$OCO_2R^h$; —$CNR''NR^oR^h$; —$NR''CNHNR^oR^h$; —$NR''C(NR^o)R^h$; —$C_{1-6}$ straight- or branched-chain alkyl, unsubstituted or substituted with one to four $R^i$ groups; —$C_{3-7}$ cycloalkyl, unsubstituted or substituted with one to four $R^i$ groups; and —$(CH_2)_nQ$ where n and Q are as defined above;

$R^n$ and $R^o$ represent hydrogen, phenyl; —$C_{1-6}$ straight- or branched-chain alkyl unsubstituted or substituted with one to four $R^i$ groups;

each $R^s$ independently represents hydrogen; phenyl or —$C_{1-6}$ straight- or branched-chain alkyl, unsubstituted or substituted with one to four $R^i$ groups;

each $R^t$ independently represents hydrogen; halo; phenyl; —CN; —$NO_2$; —$NR''R^v$; —$OR''$; —$SR''$; —$CONR''R^v$; —$COOR^h$; —$SOR''$; —$SO_2R''$; —$SO_2NR''R^v$; —$NR''SO_2R^v$; —$COR''$; —$NR''COR^v$; —$OCOR''$; —$OCONR''R^v$; —$NR''CO_2R^v$; —$NR''CONR^vR^w$; —$OCO_2R^v$; —$C_{1-6}$ straight- or branched-chain alkyl, unsubstituted or substituted with one to four $R^i$ groups;

$R^u$ and $R^v$ represent hydrogen or —$C_{1-6}$ straight- or branched-chain alkyl, unsubstituted or substituted with one to four $R^i$ groups;

each $R^w$ independently represents hydrogen; —$C_{1-6}$ straight- or branched-chain alkyl, unsubstituted or substituted with one to four $R^i$ groups; $C_{3-6}$ cycloalkyl optionally substituted with one to four $R^i$ groups; phenyl optionally substituted with one to four $R^i$ groups, or heteroaryl optionally substituted with 1–4 $R^i$ groups;

$R^x$ represents hydrogen or a $C_{1-8}$ straight- or branched-chain alkyl, optionally interrupted by one or two of O, S, SO, $SO_2$, $NR^w$, $N^+R^hR^w$, or —C(O)—, said chain being unsubstituted or substituted with one to four of halo, CN, $NO_2$, $OR^w$, $SR^w$, $SOR^w$, $SO_2R^w$, $NR^hR^w$, $N^+(R^h)_2R^w$, —C(O)—$R^w$, $C(O)NR^hR^w$, $SO_2NR^hR^w$, $CO_2R^w$, $OC(O)R^w$, $OC(O)NR^hR^w$, $NR^hC(O)R^w$, $NR^hC(O)NR^hR^w$, or a phenyl or heteroaryl group which is in turn optionally substituted with from one to four $R^i$ groups or with one to two $C_{1-3}$ straight- or branched-chain alkyl groups, said alkyl groups being unsubstituted or substituted with one to four $R^i$ groups;

$R^y$ and $R^z$ represent hydrogen; phenyl; —$C_{1-6}$ straight or branched chain alkyl, unsubstituted or substituted with one to four $R^i$ groups, and optionally interrupted by O, S, $NR^w$, $N^+R'^hR^w$ or —C(O)—;

comprising reacting a compound of formula 4':

[Structure of formula 4': bicyclic aromatic system with $(R^1)_3$ substituents, N-Sn bridge, and N-S(O)$_2$ group with N-CH$_2$ linker]

with a carbapenem of formula 7:

[Structure of formula 7: carbapenem core with OP, H$_3$C, R substituents, L leaving group, and CO$_2$P* group]

wherein R, P and P* are as previously defined and L represents a leaving group, to produce a compound of formula 6.

2. A process of synthesizing a compound of formula 4':

[Structure of formula 4']

wherein
each $R^1$ represents H, halo, OH, OP wherein P is a protecting group, —$C_{1-6}$ straight- or branched-chain alkyl, unsubstituted or substituted with one to four $R^d$ groups; and —$C_{3-7}$ cycloalkyl, unsubstituted or substituted with one to four $R^d$ groups;

each $R^d$ independently represents halo; OP, wherein P is a protecting group, —CN; —NO$_2$; —$NR^eR^f$; —$OR^g$; —$SR^g$; —$CONR^eR^f$; —$COOR^g$; —$SOR^g$; —$SO_2R^g$; —$SO_2NR^eR^f$; —$NR^eSO_2R^f$; —$COR^e$; —$NR^eCOR^f$; —$OCOR^e$; —$OCONR^eR^f$; —$NR^eCONR^fR^g$; —$NR^eCO_2R^h$; —$OCO_2R^h$; —$C(NR^e)NR^fR^g$; —$NR^eC(NH)NR^fR^g$; —$NR^eC(NR^f)R^g$; —R* or —Q;

$R^e$, $R^f$ and $R^g$ represent hydrogen; —R*; —$C_{1-6}$ straight- or branched-chain alkyl unsubstituted or substituted with one to four $R^i$ groups;

each $R^i$ independently represents halo; —CN; —NO$_2$; phenyl; —$NHSO_2R^h$; —$OR^h$, —$SR^h$; —$N(R^h)_2$; —$N^+(R^h)_3$; —$C(O)N(R^h)_2$; —$SO_2N(R^h)_2$; heteroaryl; heteroarylium; —$CO_2R^h$; —$C(O)R^h$; —$OCOR^h$; —$NHCOR^h$; guanidinyl; carbamimidoyl or ureido;

each $R^h$ independently represents hydrogen, a —$C_{1-6}$ straight or branched-chain alkyl group, a —$C_{3-C6}$ cycloalkyl group or;

Q is selected from the group consisting of wherein R* and Q are balanced by the maximum positive charges represented by R* and/or Q is two and negatively charged counterions:

[Structures of heterocyclic rings with positively charged N atoms, including 5-membered rings with α, β positions, 6-membered rings, and ammonium groups with (CH$_2$)$_a$ and (CH$_2$)$_b$ bridges, and $-NR^xR^yR^z$ group, with $L^-$ counterion]

wherein:
a and b are 1, 2 or 3;
$L^-$ is a pharmaceutically acceptable counterion;
α represents O, S or $NR^s$;
β, δ, λ, μ and σ represent $CR^t$, N or $N^+R^s$, provided that no more than one of β, δ, λ, μ and σ is $N^+R^s$;
R* is selected from the group consisting of:

[Structures of 5- and 6-membered heteroaromatic rings with positions labeled e, g, x, y, d, z]

wherein:
the maximum positive charges represented by R* and/or Q is two and
d represents O, S or $NR^k$;
e, g, x, y and z represent $CR^m$, N or $N^+R^k$, provided that no more than one of e, g, x, y and z in any given structure represents $N^+R^k$;

$R^k$ represents hydrogen; —$C_{1-6}$ straight- or branched-chain alkyl, unsubstituted or substituted with one to four $R^i$ groups; or —(CH$_2$)$_n$Q where n=1, 2 or 3 and Q is as previously defined;

each $R^m$ independently represents a member selected from the group consisting of: hydrogen; halo; —CN; —NO$_2$; —$NR''R^o$; —$OR''$; —$SR''$; —$CONR''R^o$; —$COOR^h$; —$SOR''$; —$SO_2R''$; —$SO_2NR''R^o$; —$NR''SO_2R^o$; —$COR''$; —$NR''COR^o$; —$OCOR''$; —$OCONR''R^o$; —$NR''CO_2R^h$; —$NR''CONR^oR^h$; —$OCO_2R^h$; —$CNR''NR^oR^h$; —$NR''CNHNR^oR^h$; —$NR''C(NR^o)R^h$; —$C_{1-6}$ straight- or branched-chain alkyl, unsubstituted or substituted with one to four $R^i$ groups; —$C_{3-7}$ cycloalkyl, unsubstituted or substituted with one to four $R^i$ groups; and —(CH$_2$)$_n$Q where n and Q are as defined above;

$R''$ and $R^o$ represent hydrogen, phenyl; —$C_{1-6}$ straight- or branched-chain alkyl unsubstituted or substituted with one to four $R^i$ groups;

each $R^s$ independently represents hydrogen; phenyl or —$C_{1-6}$ straight- or branched-chain alkyl, unsubstituted or substituted with one to four $R^i$ groups;

each $R^t$ independently represents hydrogen; halo; phenyl; —CN; —NO$_2$; —$NR''R^v$; —$OR''$; —$SR''$; —$CONR''R^v$; —$COOR^h$; —$SOR''$; —$SO_2R''$; —$SO_2NR''R^v$; —$NR''SO_2R^v$; —$COR''$; —$NR''COR^v$; —$OCOR''$; —$OCONR''R^v$; —$NR''CO_2R^v$; —$NR''CONR^vR^w$; —$OCO_2R^v$; —$C_{1-6}$ straight- or branched-chain alkyl, unsubstituted or substituted with one to four $R^i$ groups;

$R''$ and $R^v$ represent hydrogen or —$C_{1-6}$ straight- or branched-chain alkyl, unsubstituted or substituted with one to four $R^i$ groups;

33 each $R^w$ independently represents hydrogen; —$C_{1-6}$ straight- or branched-chain alkyl, unsubstituted or substituted with one to four $R^i$ groups; $C_{3-6}$ cycloalkyl optionally substituted with one to four $R^i$ groups; phenyl optionally substituted with one to four $R^i$ groups, or heteroaryl optionally substituted with 1–4 $R^i$ groups;

$R^x$ represents hydrogen or a $C_{1-8}$ straight- or branched-chain alkyl, optionally interrupted by one or two of O, S, SO, $SO_2$, $NR^w$, $N^+R^hR^w$, or —C(O)—, said chain being unsubstituted or substituted with one to four of halo, CN, $NO_2$, $OR^w$, $SR^w$, $SOR^w$, $SO_2R^w$, $NR^hR^w$, $N^+(R^h)_2R^w$, —C(O)—$R^w$, $C(O)NR^hR^w$, $SO_2NR^hR^w$, $CO_2R^w$, $OC(O)R^w$, $OC(O)NR^hR^w$, $NR^hC(O)R^w$, $NR^hC(O)NR^hR^w$, or a phenyl or heteroaryl group which is in turn optionally substituted with from one to four $R^i$ groups or with one to two $C_{1-3}$ straight- or branched-chain alkyl groups, said alkyl groups being unsubstituted or substituted with one to four $R^i$ groups;

$R^y$ and $R^z$ represent hydrogen; phenyl; —$C_{1-6}$ straight or branched chain alkyl, unsubstituted or substituted with one to four $R^i$ groups, and optionally interrupted by O, S, $NR^w$, $N^+R^hR^w$ or —C(O)—;

comprising reacting a compound of formula 1:

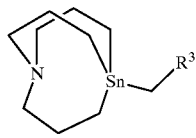

1 wherein $R^3$ is Cl, Br or I, with a naphthosultam of formula 5:

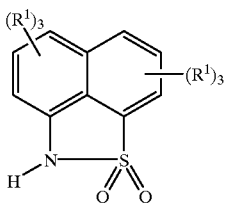

5 wherein $R^1$ is as previously defined, to produce a compound of formula 4'.

3. A process in accordance with claim 2 wherein P represents a member selected from the group consisting of: TMS triethlysilyl, TES trimethylsilyl, TBDMS t-butyldimethylsilyl, o-nitrobenzyloxycarbonyl, p-nitrobenzyloxycarbonyl, benzyloxycarbonyl, allyloxycarbonyl, t-butyloxycarbonyl and 2,2,2-trichloroethyloxycarbonyl.

4. A process in accordance with claim 2 wherein P* represents a member selected from the group consisting of: allyl, benzhydryl, 2-naphthylmethyl, benzyl, silyl groups such as t-butyldimethylsilyl (TBDMS), trimethylsilyl, (TMS), triethylsilyl (TES), phenacyl, p-methoxybenzyl, o-nitrobenzyl, p-methoxyphenyl, p-nitrobenzyl, 4-pyridylmethyl and t-butyl.

5. A process in accordance with claim 2 wherein R represents methyl.

6. A process in accordance with claim 2 wherein L represents a member selected from the group consisting of: OMs, OTs, OTf, halo and diphenylphosphonyl.

7. A process in accordance with claim 2 wherein $R^3$ represents I and at least one $R^1$ represents a —$C_{1-6}$ straight

34 or branched chain alkyl group, substituted with one to four $R^d$ groups, wherein one $R^d$ group represents —R* or Q wherein R* and Q are balanced by the maximum positive charges represented by R* and/or Q is two and negatively charged counterions.

8. A process of synthesizing a compound of formula 4:

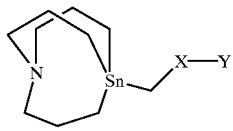

4 wherein

X and Y taken in combination represent a ring system containing from 0–3 nitrogen atoms and 0–2 heteroatoms selected from O, S, S(O) and S(O)$_2$, said ring system having 1–4 rings, with from 5–16 atoms, said system being non-aromatic, partially aromatic or aromatic, and being unsubstituted or substituted with from 1–3 groups selected from halo, OH, OP, wherein P is a protecting group, $C_{1-6}$ alkyl and $C_{1-6}$ alkyl substituted with from 1–3 of halo, OH, OP, $NH_2$, $NHC_{1-4}$ alkyl and $N(C_{1-4}$ alkyl)$_2$ comprising reacting compound 1:

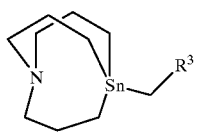

1 wherein $R^3$ is Cl, Br or I, with a compound of the formula M-X-Y wherein M represents H or a metal cation, and X and Y are as previously defined, to produce a compound of formula 4.

9. A process in accordance with claim 8 wherein $R^3$ represents and least one $R^1$ represents a —$C_{1-6}$ straight or branched chain alkyl group, substituted with one to four $R^d$ groups, wherein one $R^d$ group represents —R* or Q wherein R* and Q are balanced by the maximum positive charges represented by R* and/or Q is two and negatively charged counterions.

10. A process in accordance with claim 9 wherein $R^3$ represents Cl and at least one $R^1$ represents a —$C_{1-6}$ straight or branched chain alkyl group, substituted with one to four $R^d$ groups, wherein one $R^d$ group represents —R* or Q wherein R* and Q are balanced by the maximum positive charges represented by R* and/or Q is two and negatively charged counterions.

11. A process in accordance with claim 7 wherein $R^3$ represent Cl and at least one $R^1$ represents a —$C_{1-6}$ straight or branched chain alkyl group, substituted with one to four $R^d$ groups, wherein one $R^d$ group represents —R* or Q wherein R* and Q are balanced by the maximum positive charges represented by R* and/or Q is two and negatively charged counterions.

12. A compound represented by one of the following formulas:

wherein $R^3$ is Cl, Br or I;

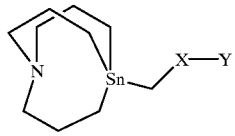

4 wherein

X represents and Y represents H or a protecting group, or X and Y taken in combination represent a ring system containing from 0–3 nitrogen atoms and 0–2 heteroatoms selected from O, S, S(O) and $S(O)_2$, said ring system having 1–4 rings, with from 5–16 atoms, said system being non-aromatic, partially aromatic or aromatic, and being unsubstituted or substituted with from 1–3 groups selected from halo, OH, OP, wherein P is a protecting group, $C_{1-6}$ alkyl and $C_{1-6}$ alkyl substituted with from 1–3 of halo, OH, OP, $NH_2$, $NHC_{1-4}$ alkyl and $N(C_{1-4}$ alkyl$)_2$ or

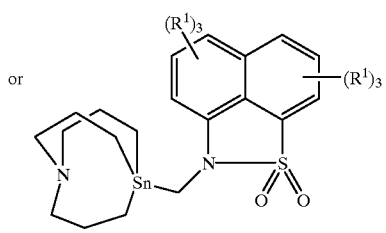

4' wherein each $R^1$ represents H, halo, OH, OP wherein P is a protecting group, —$C_{1-6}$ straight- or branched-chain alkyl, unsubstituted or substituted with one to four $R^d$ groups; and —$C_{3-7}$ cycloalkyl, unsubstituted or substituted with one to four $R^d$ groups;

each $R^d$ independently represents halo; OP, wherein P is a protecting group, —CN; —$NO_2$; —$NR^eR^f$; —$OR^g$; —$SR^g$; —$CONR^eR^f$; —$COOR^g$; —$SOR^g$; —$SO_2R^g$; —$SO_2NR^eR^f$; —$NR^eSO_2R^f$; —$COR^e$; —$NR^eCOR^f$; —$OCOR^e$; —$OCONR^eR^f$; —$NR^eCONR^fR^g$; —$NR^eCO_2R^h$; —$OCO_2R^h$; —$C(NR^e)NR^fR^g$; —$NR^eC(NH)NR^fR^g$; —$NR^eC(NR^f)R^g$; —R* or —Q;

each $R^i$ independently represents halo; —CN; —$NO_2$; phenyl; —$NHSO_2R^h$; —$OR^h$, —$SR^h$; —$N(R^h)_2$; —$N^+(R^h)_3$; —$C(O)N(R^h)_2$; —$SO_2N(R^h)_2$; heteroaryl; heteroarylium; —$CO_2R^h$; —$C(O)R^h$; —$OCOR^h$; —$NHCOR^h$; guanidinyl; carbamimidoyl or ureido;

each $R^h$ independently represents hydrogen, a —$C_{1-6}$ straight or branched-chain alkyl group, a —$C_3$-$C_6$ cycloalkyl group or phenyl, or when two $R^h$ groups are present, said $R^h$ groups may be taken in combination and represent a 4–6 membered saturated ring, optionally interrupted by one or two of O, S, $SO_2$, —C(O)—, NH and $NCH_3$, Q is selected from the group consisting of wherein R* and Q are balanced by the maximum positive charges represented by R* and/or Q is two and negatively charged counterions:

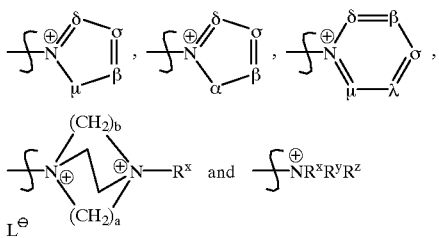

wherein:

a and b are 1, 2 or 3;
$L^-$ is a pharmaceutically acceptable counterion;
α represents O, S or $NR^s$;
β, δ, λ, μ and σ represent $CR^t$, N or $N^+R^s$, provided that no more than one of β, δ, λ, μ and σ is $N^+R^s$;
R* is selected from the group consisting of:

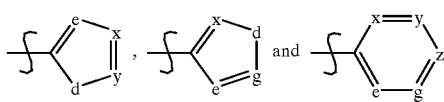

wherein:
d represents O, S or $NR^k$;
e, g, x, y and z represent $CR^m$, N or $N^+R^k$, provided that no more than one of e, g, x, y and z in any given structure represents $N^+R^k$;

$R^k$ represents hydrogen; —$C_{1-6}$ straight- or branched-chain alkyl, unsubstituted or substituted with one to four $R^i$ groups; or —$(CH_2)_nQ$ where n=1, 2 or 3 and Q is as previously defined;

each $R^m$ independently represents a member selected from the group consisting of: hydrogen; halo; —CN; —$NO_2$; —$NR''R^o$; —$OR''$; —$SR''$; —$CONR''R^o$; —$COOR^h$; —$SOR''$; —$SO_2R''$; —$SO_2NR''R^o$; —$NR''SO_2R^o$; —$COR''$; —$NR''COR^o$; —$OCOR''$; —$OCONR''R^o$; —$NR''CO_2R^h$; —$NR''CONR^oR^h$; —$OCO_2R^h$; —$CNR''NR^oR^h$; —$NR''CNHNR^oR^h$; —$NR''C(NR^o)R^h$; —$C_{1-6}$ straight- or branched-chain alkyl, unsubstituted or substituted with one to four $R^i$ groups; —$C_{3-7}$ cycloalkyl, unsubstituted or substituted with one to four $R^i$ groups; and —$(CH_2)_nQ$ where n and Q are as defined above;

$R''$ and $R^o$ represent hydrogen, phenyl; —$C_{1-6}$ straight- or branched-chain alkyl unsubstituted or substituted with one to four $R^i$ groups;

each $R^s$ independently represents hydrogen; phenyl or —$C_{1-6}$ straight- or branched-chain alkyl, unsubstituted or substituted with one to four $R^i$ groups;

each $R^t$ independently represents hydrogen; halo; phenyl; —CN; —$NO_2$; —$NR''R^v$; —$OR''$; —$SR''$; —$CONR''R^v$; —$COOR^h$; —$SOR''$; —$SO_2R''$; —$SO_2NR''R^v$; —$NR''SO_2R^v$; —$COR''$; —$NR''COR^v$; —$OCOR''$; —$OCONR''R^v$; —$NR''CO_2R^v$; —$NR''CONR^vR^w$; —$OCO_2R^v$; —$C_{1-6}$ straight- or branched-chain alkyl, unsubstituted or substituted with one to four $R^i$ groups;

$R''$ and $R^v$ represent hydrogen or —$C_{1-6}$ straight- or branched-chain alkyl, unsubstituted or substituted with one to four $R^i$ groups;

each $R^w$ independently represents hydrogen; —$C_{1-6}$ straight- or branched-chain alkyl, unsubstituted or substituted with one to four $R^i$ groups; $C_{3-6}$ cycloalkyl optionally substituted with one to four $R^i$ groups; phenyl optionally substituted with one to four $R^i$ groups, or heteroaryl optionally substituted with 1–4 $R^i$ groups;

$R^x$ represents hydrogen or a $C_{1-8}$ straight- or branched-chain alkyl, optionally interrupted by one or two of O, S, SO, $SO_2$, $NR^w$, $N^+R^hR^w$, or —C(O)—, said chain being unsubstituted or substituted with one to four of halo, CN, $NO_2$, $OR^w$, $SR^w$, $SOR^w$, $SO_2R^w$, $NR^hR^w$, $N^+(R^h)_2R^w$, —C(O)—$R^w$, C(O)$NR^hR^w$, $SO_2NR^hR^w$, $CO_2R^w$, OC(O)$R^w$, OC(O)$NR^hR^w$, $NR^hC(O)R^w$, $NR^hC(O)NR^hR^w$, or a phenyl or heteroaryl group which is in turn optionally substituted with from one to four $R^i$ groups or with one to two $C_{1-3}$ straight- or branched-chain alkyl groups, said alkyl groups being unsubstituted or substituted with one to four $R^i$ groups;

$R^y$ and $R^z$ represent hydrogen; phenyl; —$C_{1-6}$ straight or branched chain alkyl, unsubstituted or substituted with one to four $R^i$ groups, and optionally interrupted by O, S, $NR^w$, $N^+R^hR^w$ or —C(O)—.

13. A compound having the following structure:

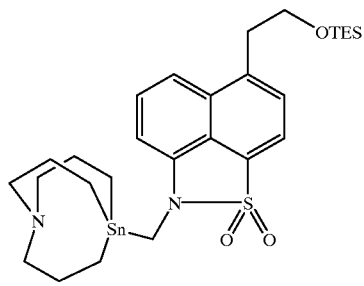

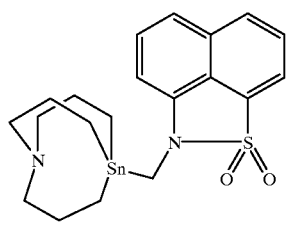

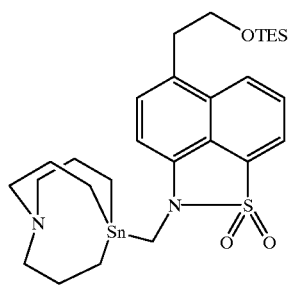

-continued

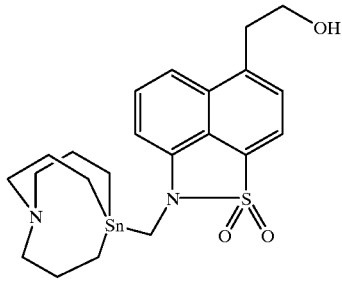

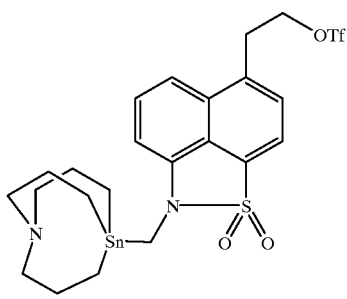

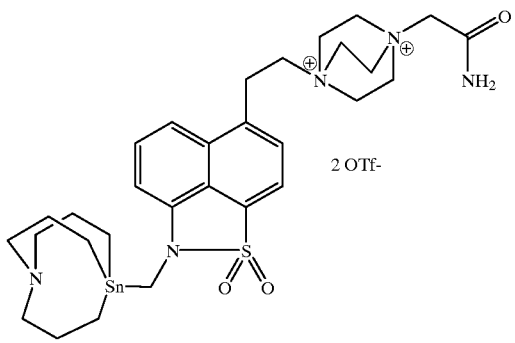

and

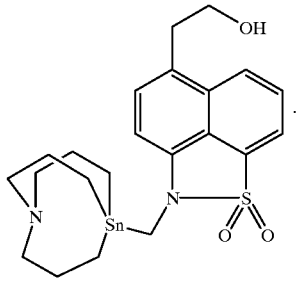

* * * * *